(12) United States Patent
Ueda

(10) Patent No.: US 8,315,688 B2
(45) Date of Patent: Nov. 20, 2012

(54) MEDICAL IMAGE MANAGEMENT SYSTEM AND MEDICAL IMAGE MANAGEMENT METHOD

(75) Inventor: Atsuhiro Ueda, Kobe (JP)

(73) Assignee: Seventh Dimension Design, Inc., Chuo-ku, Kobe-shi Hyogo (JP)

( * ) Notice: Subject to any disclaimer, the term of this patent is extended or adjusted under 35 U.S.C. 154(b) by 1352 days.

(21) Appl. No.: 11/643,736

(22) Filed: Dec. 21, 2006

(65) Prior Publication Data

US 2007/0225574 A1    Sep. 27, 2007

(51) Int. Cl.
*A61B 5/04* (2006.01)
(52) U.S. Cl. ......... 600/407; 600/300; 128/920; 128/923
(58) Field of Classification Search ................... 600/300, 600/407; 128/920, 923; 705/2; 434/236
See application file for complete search history.

(56) References Cited

U.S. PATENT DOCUMENTS

2004/0072133 A1*  4/2004  Kullok et al. ................ 434/236
2005/0278195 A1*  12/2005  Getz ................................ 705/2

FOREIGN PATENT DOCUMENTS

JP       2002-058641       2/2002

OTHER PUBLICATIONS

Goldman, L, et al, Stresses affecting surgical performance and learning: I. Correlation of heart rate, electrocardiogram, and operation simultaneously recorded on videotapes., Journal of Surgical Research, vol. 12, issue 2, Feb. 1972, abstract.*
Goldman, L. et al.; "Stresses Affecting Surgical Performance and Learning"; Journal of Surgical Research; vol. 12, pp. 83-86; Academic Press Inc.; 1972.

* cited by examiner

*Primary Examiner* — Brian Casler
*Assistant Examiner* — Daniel Huntley
(74) *Attorney, Agent, or Firm* — Larry E. Henneman, Jr.; Henneman & Associates, PLC

(57) ABSTRACT

A medical image management system includes: a medical imaging device for imaging a patient to receive a medical treatment and creating a medical moving picture; and a recording unit for recording the medical moving picture imaged by the medical imaging device. The system further includes: a measurement unit for measuring biological information on a person who performs the medical treatment; and an indexing unit for adding an index to the medical moving picture recorded in the recording unit, according to the measurement result obtained by the measurement unit. By providing this system, it is possible to add an index to the medical moving picture recorded, according to the change of the biological information on the person who performs medical treatment on a patient.

32 Claims, 15 Drawing Sheets

(a)

(b)

(c)

MEDICAL IMAGE MANAGEMENT SYSTEM AND MEDICAL IMAGE MANAGEMENT METHOD

CROSS REFERENCE TO RELATED APPLICATIONS

This application claims the right of priority under 35 U.S.C. §120, as authorized by 35 U.S.C. §365(c), to International Application No. PCT/JP2004/008991, filed on Jun. 25, 2004 by the same inventor (published under PCT Article 21(2) in Japanese and not English), which is incorporated herein by reference in it's entirety.

BACKGROUND OF THE INVENTION

1. Technical Field

The present invention relates to a medical image management system and a medical image management method. The present invention particularly relates to a medical image management system and a medical image management method that can add indices to the recorded medical movies according to the physiological data of a surgeon who performs medical treatment on a patient.

2. Description of the Related Art

Conventionally, movies of a surgery are captured by surgical cameras such as endoscopes and microscopes for ophthalmic surgeries. The in-vivo images are displayed on a screen of an output device while recorded in a recording medium as movie information. The movie of the medical treatment (medical movie) is recorded and saved for helping to recall important events during a surgery more vividly and accurately than other events among many surgical records.

Recently, a device capable of capturing still-image information (still image) from the recorded movie information (movie) during a surgery has been developed. When an event of high importance occurs, a person who performs medical treatment captures still images by operating some recording device.

The invention disclosed in Japanese Publication No. 2002-58641 includes a foot switch to be used for a surgeon to efficiently capture still images during a surgery. The surgeons can easily and efficiently capture the still images during their surgery by operating the foot switch with their foot.

The above-mentioned invention enables a surgeon to sample still images without any interruption during a surgery because they can capture desired still images by using the foot switch.

While the foot switch enables the surgeon to capture the desired still-images, if the surgeon forgets to operate the foot switch, the images cannot be obtained. Moreover, unless the surgeon decides to capture still images, nothing will be obtained.

The above-mentioned device for capturing still images depends on the surgeon's will whether to capture still images. However, the surgeon concentrating his attention to a surgery tends to forget to operate a footswitch or the like to capture still images.

The conventional imaging devices are not helpful in knowing how surgeons react to a specific situation.

Particularly, it is difficult to direct his attention to capturing still images with the conventional method while performing medical treatment, especially during such a stressful event that it causes changes in the physiological data of the surgeon.

It is also significantly difficult to tell stressful situations for an inexperienced surgeon. It is also difficult to tell what medical event makes him confused. Thus, he does not understand what stressful situation he will meet in a surgery room until he is involved in actual medical treatment.

Considering the above, there has been a need for a medical image management system configured to capture still images not depending on the surgeon's will but on the surgeons' physiological data corresponding to his stress level.

Furthermore, when the physiological conditions of the surgeons are measured, the resultant physiological data usually has non-linear changes rather than linear-changes in chronological order. Therefore, it is difficult to use the physiological data to make an accurate decision about when the surgeons become nervous.

The present invention relates to a medical image management system and a medical image management method that are capable of adding indices to a recorded medical movie according to the changes in the physiological data of a person who performs medical treatment.

SUMMARY OF INVENTION

According to the present invention, there is provided a medical image management system comprising: a medical imaging device configured to capture a medical movie of a patient who receives medical treatment, the medical movie consisting of a plurality of still images; a recording means configured to record the movie captured with the medical imaging device, wherein the medical image management system further includes: a measurement means configured to measure physiological conditions of a surgeon who performs medical treatment on the patient and to obtain physiological data; and an indexing means configured to add indices to the medical movie recorded by the recording means.

In one embodiment of the present invention, the indexing means comprises: a data receiving means configured to receive the physiological data from the measurement means; a comparison means configured to compare the physiological data received by the data receiving means with a predetermined threshold, and a first sampling means configured to sample still-image information from the movie if the first comparison means detects that the physiological data exceeds the threshold, wherein the still-image information is sampled by the first sampling means from a still image of the moment when the physiological data exceeds the threshold.

In one embodiment of the present invention, the indexing means further comprises a first start-and-end-index-recording means configured to record the still-image information sampled by the first sampling means as start-index information of the medical movie in the recording means, wherein, if the first comparison means detects that the physiological data falls below the threshold after the first sampling means samples the still-image information, the first start-and-end-index-recording means samples still-image information from the medical movie recorded in the recording means and records the still-image information as end-index information of the medical movie in the recording means, wherein the still-image information is sampled by the first start-and-end-index-recording means from a still image of the moment when the physiological data falls below the threshold.

In one embodiment of the present invention, the indexing means includes: a data receiving means configured to receive physiological data obtained by the measurement means; a physiological-data-saving means configured to save the physiological data received by the data receiving means in chronological order; a difference-value-calculating means configured to calculate a chronological difference-value based on adjacent two of the physiological data saved in the physiological-data-saving means; a second comparison means configured to compare the difference-value calculated by the difference-value-calculating means with a predetermined difference-value; and a second sampling means configured to sample still-image information from the medical movie if the second comparison means detects that the calculated difference-value exceeds the predetermined difference-value, wherein the still-image information is sampled by the second sampling means from a still image of the moment when the older physiological data of the adjacent two of physiological data that are used to calculate the difference-value.

In one embodiment of the present invention, the indexing means further comprises a second start-and-end-index-recording means configured to record the still-image information sampled by the second sampling means as start-index information of the medical movie in the recording means, wherein, if the second comparison means detects that the physiological data falls below the threshold after the second sampling means samples the still-image information, the second start-and-end-index-recording means (58) samples still-image information from the medical movie recorded in the recording means and records the still-image information as end-index-information of the medical movie in the recording means, and wherein the still-image information is sampled by the second start-and-end-index-recording means from a still image of the moment when the physiological data falls below the threshold.

In one embodiment of the present invention, the medical image management system further comprises an index-adjusting means configured to shift back the start-index information by a predetermined time length and to shift forward the end-index information by a predetermined time length.

In one embodiment of the present invention, still-image information to be recorded as the start-index information and/or after the end-index information is continuously sampled for a predetermined time length before and/or the first sampling means and the second sampling means (58) samples the still-image information.

In one embodiment of the present invention, the medical movie and/or the still-images saved in the recording means from when the start-index information is sampled and recorded in the recording means (4) to when the end-index information is sampled and recorded in the recording means.

In one embodiment of the present invention, the medical image management system further includes: a separating means configured to separate a plurality of chronologically-ordered still images from the medical movie recorded in the recording means; a calculating means configured to calculate coordinate values in a color space of each still image that is separated by the separating means; a selecting means configured to select adjacent two of the still images if the difference between the coordinate values of the two still images exceeds a predetermined threshold, an adding means configured to add image difference information to each of the still images selected by the selecting means.

In one embodiment of the present invention, the medical image management system further comprises an output means comprising: a first display configured to display the medical movie captured with the medical imaging device; and a second display configured to display the still images sampled by the first sampling means and the second sampling means.

In one embodiment of the present invention, the measurement means is configured to measure at least one physiological parameter selected from a group consisting of the surgeon's heart beat, blood pressure, sweat production, body temperature, electroencephalogram, grip strength, point of gaze, blink, pupil, eye movement, respiratory rate (including apneic period), pneumogram, number of swallowing, skin electric conductance, electric potential difference of muscle, neurotransmitter level, blood glucose level, blood flow rate, blood composition, amount of various hormones, chewing pressure, electrocardiogram, galvanic skin reflex, fingertip pulse wave, posture or position, tear production, tear composition, saliva production, saliva composition, gastric secretion, gastric fluid composition, facial expression (measurement in characteristic analysis), vocal change (measurement in characteristic analysis), lip reading (measurement in characteristic analysis), limb shivering, urine (protein level, sugar level, occult blood level).

In one embodiment of the present invention, all of the physiological data obtained by the measurement means is recorded in the recording means together with the medical movie that chronologically corresponds to the physiological data.

In one embodiment of the present invention, the medical image management system is further configured to select movies to which a larger number of the indices are added from the plurality of medical movies recorded in the recording means, and to carry out a predetermined process on the selected medical movies.

In one embodiment of the present invention, the medical image management further includes a manual indexing means configured to enable the surgeon to add indices to the medical movies.

According to the present invention, there is further provided a medical image management method of producing a medical movie of a patient who receives medical treatment and of managing the medical movie, the method including steps of: recording the medical movies while obtaining physiological data of a surgeon; and adding indices to the medical movie according to the physiological data of the surgeon.

In one embodiment of the present invention, the indices are added to the medical movies according to a comparison between the obtained physiological data and a threshold or according to a chronological change in the obtained physiological data.

In one embodiment of the present invention, the step of adding indices includes a step of sampling still-image information of still images contained in the medical movie.

In one embodiment of the present invention, the medical movie management method further includes steps of: calculating the moments to start sampling and to stop sampling the medical movie based on two of the sampled still-image information; and sampling and recording the medical movie or still images contained in the medical movie captured between the calculated moments.

In one embodiment of the present invention, the medical image management method further includes a step of simultaneously displaying the medical movie captured by the medical imaging device and the medical movie sampled according to the physiological data of the surgeon.

In one embodiment of the present invention, the physiological data of the surgeon includes at least one parameter selected from a group consisting of the surgeon's heart beat, blood pressure, sweat production, body temperature, electroencephalogram, grip strength, point of gaze, blink, pupil, eye movement, respiratory rate (including apneic period), pneumogram, number of swallowing, skin electric conductance, electric potential difference of muscle, neurotransmitter level, blood glucose level, blood flow rate, blood composition, amount of various hormones, chewing pressure, electrocardiogram, galvanic skin reflex, fingertip pulse wave, posture or position, tear production, tear composition, saliva production, saliva composition, gastric secretion, gastric fluid composition, facial expression (measurement in characteristic analysis), vocal change (measurement in characteristic analysis), lip reading (measurement in characteristic analysis), limb shivering, urine (protein level, sugar level, occult blood level).

In one embodiment of the present invention, information about events that occur during medical treatment is saved in the medical movies.

In one embodiment of the present invention, the medical image management method further includes a step of selecting a certain medical movie depending on the total number of the indices added to the medical movie.

In one embodiment of the present invention, the medical image management method further includes a step of adding indices to the medical movies according to the operation by the surgeon.

According to one embodiment of the present invention, the medical image management system adds indices to a medical movie according to changes in the physiological data of a surgeon who performs the medical treatment on a patient. Using the medical image management system, one can understand the changes in the surgeon's mental condition. For example, the indices added to the movie facilitate to pick up the stressful events for the surgeon. It is also possible to manage data about stressful events for an inexperienced surgeon. Such data can be used to give effective instructions to other surgeons. By using the device, it is further possible to know both important events and stressful events for the surgeon. This helps to provide safe medical treatment on patients and to improve the rate of successful treatment.

According to another embodiment of the present invention, the medical image management system adds indices to the medical movie if the obtained physiological data exceeds a predetermined threshold.

According to another embodiment of the present invention, the medical image management system provides the recorded medical movie with start indices and end indices that indicate supposedly important scenes of the medical treatment.

According to another embodiment of the present invention, the medical image management system uses chronological difference values to accurately detect changes in the physiological data and to add indices to the medical movie according to the detected changes.

According to another embodiment of the present invention, the medical image management system provides the recorded medical movie with start indices and end indices that indicate supposedly important scenes of the medical treatment.

According to another embodiment of the present invention, the medical image management system appropriately shifts indices to play a medical movie having an appropriate time length.

According to another embodiment of the present invention, the medical image management system samples a medical movie or a group of still images as start-index information and end-index information.

According to another embodiment of the present invention, the medical image management system saves a medical movie or a group of still images showing the important scenes of the medical treatment in the recording means (4) using the index information.

According to another embodiment of the present invention, the medical image management system detects changes in the still images contained in the medical movie by using coordinate values in color spaces of the still images.

According to another embodiment of the present invention, the medical image management system includes a first display (A) and a second display (C) so that the user can view the medical movies and the still images sampled from the medical movies.

According to another embodiment of the present invention, the medical image management system uses data of surgeon's heart beat, blood pressure, sweat production, body temperature, electroencephalogram, grip strength, point of gaze, blink, pupil, eye movement, respiratory rate (including apneic period), pneumogram, number of swallowing, skin electric conductance, electric potential difference of muscle, neurotransmitter level, blood glucose level, blood flow rate, blood composition, amount of various hormones, chewing pressure, electrocardiogram, galvanic skin reflex, fingertip pulse wave, posture or position, tear production, tear composition, saliva production, saliva composition, gastric secretion, gastric fluid composition, facial expression (measurement in characteristic analysis), vocal change (measurement in characteristic analysis), lip reading (measurement in characteristic analysis), limb shivering, urine (protein level, sugar level, occult blood level) to effectively estimate the physiological condition of the surgeon and to add index information to the medical movie.

According to another embodiment of the present invention, the medical image management system efficiently records and saves the medical movie based on various kinds of physiological data.

According to another embodiment of the present invention, the medical image management system prioritize medical movies based on the indices added to each medical movie. After being given priority, the medical movies are subjected to different processes according to their level of priority.

According to another embodiment of the present invention, the medical image management system enables the surgeon to sample medical images including still images and movies. Thus, both medical images sampled by the medical image management system and the medical movies sampled by the surgeon can be used to examine the importance of various scenes of the medical movie from different points of view.

According to another embodiment of the medical treatment method of the present invention, it is possible to add indices to a medical movie based on changes in the physiological data of the surgeon who performs the medical treatment on a patient. Using the medical image management method, one can estimate the changes in the surgeon's mental condition. For example, the indices added to the movie facilitate to pick up the stressful events for the surgeon. It is also possible to manage data about stressful events for an inexperienced surgeon. Such data can be used to give effective instructions to other surgeons. By using the device, it is further possible to know both important events and stressful events for the surgeon. This helps to provide safe medical treatment on patients and to improve the rate of successful treatment.

According to another embodiment of the medical image management method of the present invention, it is possible to add effective indices to the medical movie based on changes in the difference value of the physiological data.

According to another embodiment of the medical image management method of the present invention, what is sampled as indices are not the still images but the information (still image information) about the still images. This helps to reduce memory size engaged in the management of the medical images.

According to another embodiment of the medical image management method of the present invention, it is possible to sample a medical movie or still images from the medical movie showing the scenes that the user considers important by using still image information.

According to another embodiment of the medical image management method of the present invention, as a medical movie and still images to which indices are added are displayed simultaneously, the user can easily manage the medical images.

According to another embodiment of the medical image management method of the present invention, it is possible to effectively estimate the physiological condition of the surgeon and to add index information to the medical movie by using the data of surgeon's heart beat, blood pressure, sweat production, body temperature, electroencephalogram, grip strength, point of gaze, blink, pupil, eye movement, respiratory rate (including apneic period), pneumogram, number of swallowing, skin electric conductance, electric potential difference of muscle, neurotransmitter level, blood glucose level, blood flow rate, blood composition, amount of various hormones, chewing pressure, electrocardiogram, galvanic skin reflex, fingertip pulse wave, posture or position, tear production, tear composition, saliva production, saliva composition, gastric secretion, gastric fluid composition, facial expression (measurement in characteristic analysis), vocal change (measurement in characteristic analysis), lip reading (measurement in characteristic analysis), limb shivering, urine (protein level, sugar level, occult blood level).

According to another embodiment of the medical image management method of the present invention, it is possible to record information about the events that occur during the medical treatment, such as information about when the surgeon or medical personnel enters and leaves the room in which the medical treatment is carried out.

According to another embodiment of the medical image management method of the present invention, it is possible to prioritize the medical movies based on the indices added to each medical movie. After the prioritization, the medical movies are subjected to different processes according to their priority level.

According to another embodiment of the medical image management method of the present invention, the surgeon can sample medical images (i.e. still images and movies). Thus, both medical images sampled by the medical image management system and the medical images sampled by the surgeon can be used to examine the importance of various scenes of the medical movie from different points of view.

BRIEF DESCRIPTION OF THE DRAWINGS

The preferred embodiments of the medical image management system of the present invention will be described below referring to the accompanying drawings.

DESCRIPTION OF THE INVENTION

The term "surgeon" used herein refers to a person who performs medical treatment on a patient. Surgeons include any persons who are concerned in a surgery, such as persons who partake in a surgery (e.g. surgeons and anesthesists), persons who help the surgeon, nurses, and pharmacists, but not limited to these. In the description below, examples where one surgeon is involved are explained but the number of the surgeons is not particularly limited. If several surgeons are involved in a surgery, the physiological data of all of the surgeons is preferably obtained.

The term "physiological data" refers to data obtained by measuring at least one physiological parameter selected from a group consisting of surgeon's heart beat, blood pressure, sweat production, body temperature, electroencephalogram, grip strength, point of gaze, blink, pupil, eye movement, respiratory rate (including apneic period), pneumogram, number of swallowing, skin electric conductance, electric potential difference of muscle, neurotransmitter level, blood glucose level, blood flow rate, blood composition, amount of various hormones, chewing pressure, electrocardiogram, galvanic skin reflex, fingertip pulse wave, posture or position, tear production, tear composition, saliva production, saliva composition, gastric secretion, gastric fluid composition, facial expression (measurement in characteristic analysis), vocal change (measurement in characteristic analysis), lip reading (measurement in characteristic analysis), limb shivering, and urine (protein level, sugar level, occult blood level). The chronological changes in these physiological data are recorded with a measurement means described below.

The term "Measurements in a characteristic analysis" refers to the amount of chronological changes (difference value) in the physiological data. The change in this difference value represents the characteristics of the physiological data.

The medical image management system and the medical image management method of the present invention collect the physiological data from the surgeon. Preferably, physiological data of a patient is measured in addition to that of the surgeon. If there are several patients involved in the medical treatment, physiological data of all the patients is preferably collected.

Figure 2:
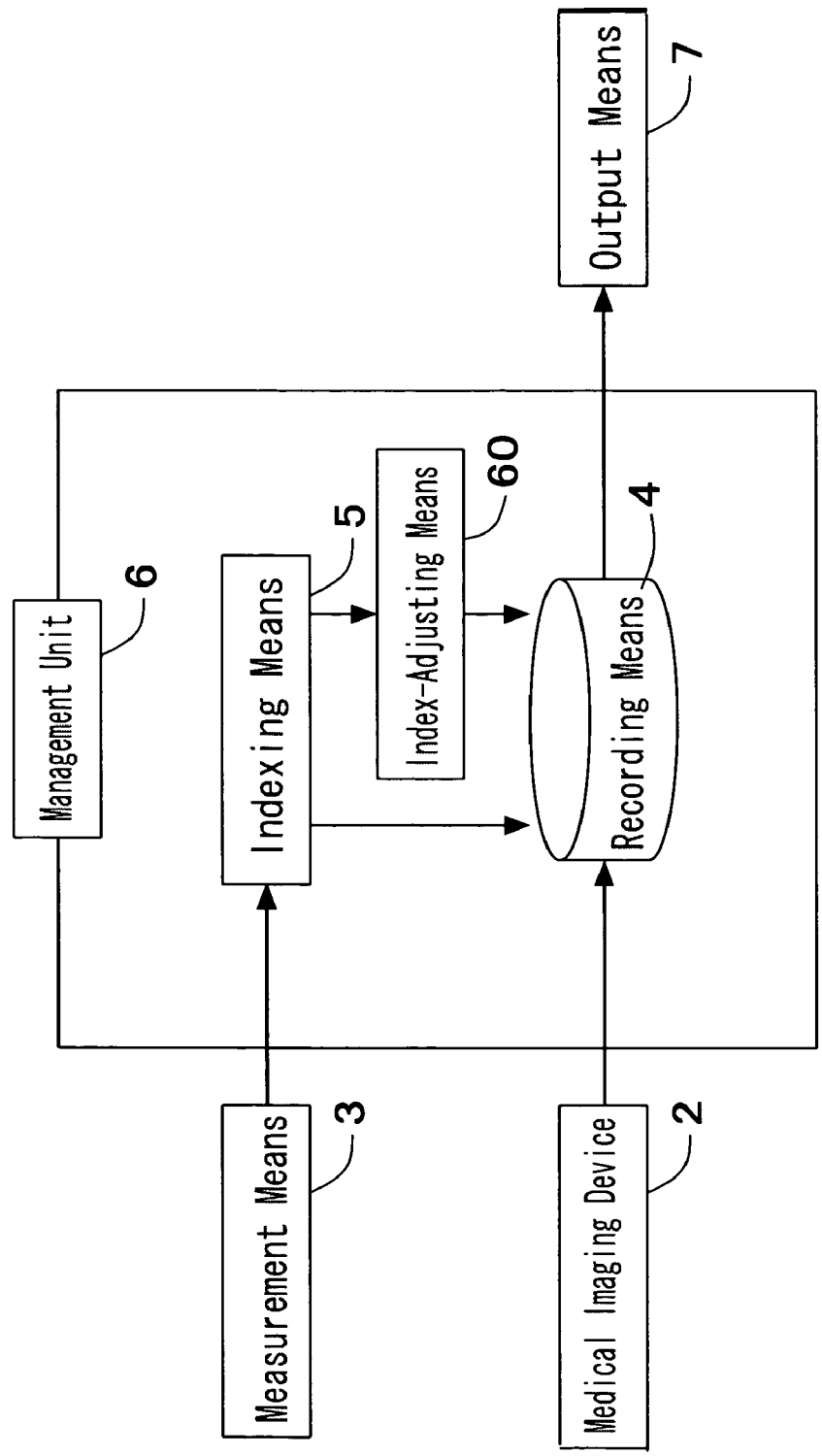
FIG. 2 is a block diagram illustrating the configuration of the medical image management device of the present invention.

The medial image management system (1) of the present invention includes a management unit (6). The management unit (6) includes a medical imaging device (2), a measurement means (3), a recording means (4), and an indexing means (5) (See FIG. 2).

The medical imaging device (2) includes, for example, an imaging device configured to capture a movie of medical treatment performed by the surgeon and an imaging device configured to capture a movie of the patient's body site subjected to the medical treatment. These medical imaging devices are preferably used for the present invention. The medical device (2) includes analog or digital medical imaging devices such as surgical microscopes and cameras configured to capture an operative field.

The measurement means (3) is used for measuring physiological conditions and for sending the data about the physiological conditions to the management unit (6) described below. The measurement means (3) is attached to the surgeon's body during the use. The measurement means (3) is designed not to disturb the surgeon's medical treatment.

Figure 1:
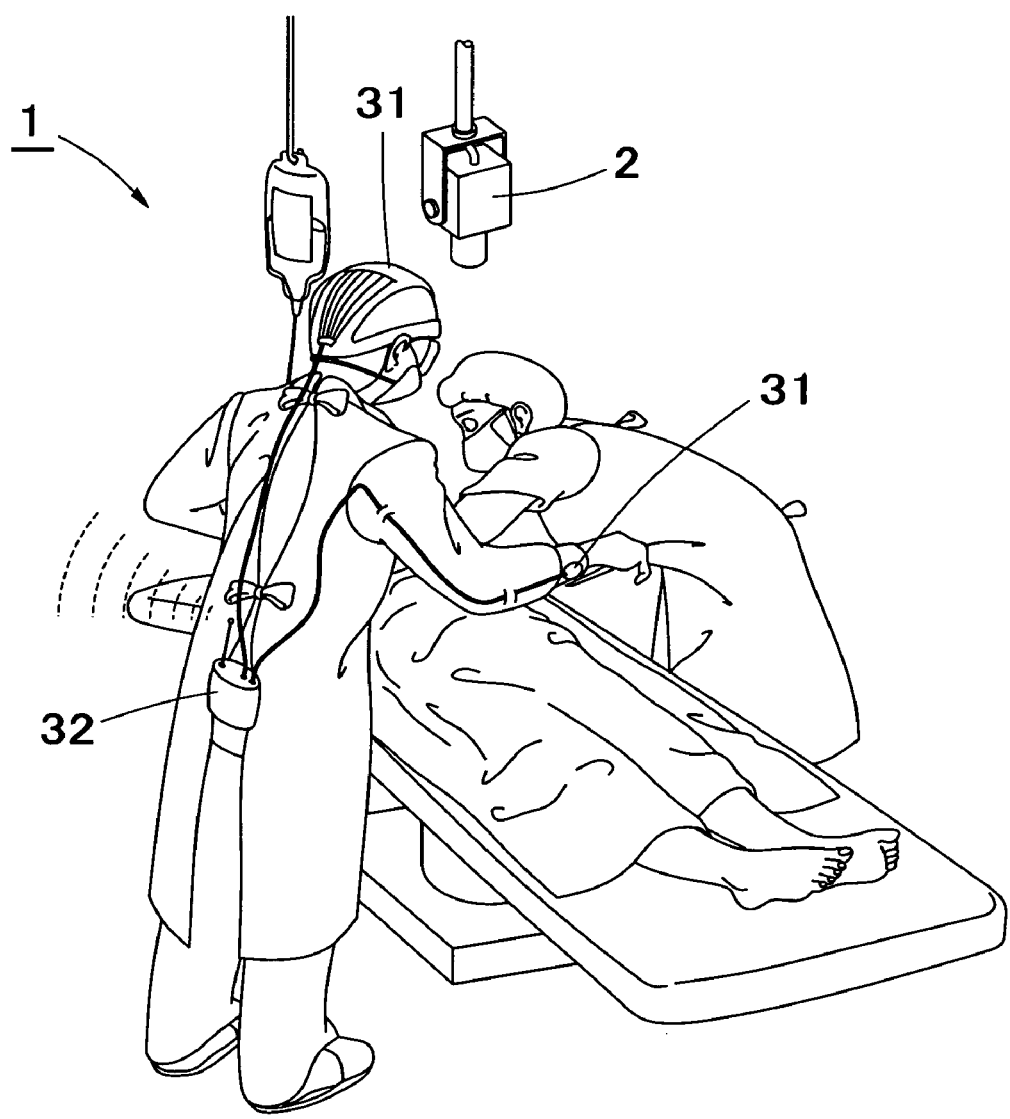
FIG. 1 is a view illustrating the medical treatment using the present invention.

The measurement means (3) shown in FIG. 1 includes measuring parts (31) configured to measure the surgeon's electroencephalogram and his blood pressure. After measuring the electroencephalogram and the blood pressure, the measuring parts (31) send these physiological data to a sending part (sender) (32). In the example of FIG. 1, the sending part (32) sends these information to the management unit (6) using a radio system. However, the physiological data may be transmitted to the management unit (6) through any radio communication or any wired communication.

Any transmission mode may be also used as long as it does not disturb the surgeon. The measurement means (3) may be equipped elsewhere than the surgeon's body. In this case, any measuring instrument that accurately measures the physiological conditions is applicable.

The management unit (6) is comprised of a recording means (4) and an indexing means (5) described below. The management unit (6) may be a common commercial computer that includes an input device (e.g. a keyboard and a mouse); an arithmetic unit configured to perform calculations (e.g. addition, subtraction, multiplication and division) and comparison; a memory unit configured to temporarily save the calculation results; a display unit configured to displaying medical movies and medical still images; a control unit configured to control these units. These functionalities are helpful in performing the processes described below.

The recording means (4) in the management unit (6) may be either an internal main memory or an external memory. The recording means (4) receives and records therein the medical movies captured by the medical imaging device (2). The medical movies are recorded together with information about the time when the movies are recorded.

The indexing means (5) in the management unit (6) performs the following processes. The indexing means (5) adds indices to the medical movies recorded in the recording means (4) according to the physiological data obtained by the measurement means (3). The indices are recorded in the recording means (4) together with the medical movies.

Methods of adding indices to the medical movie with the indexing means (5) are described below.

Firstly, the first indexing method is described.

Figure 3:
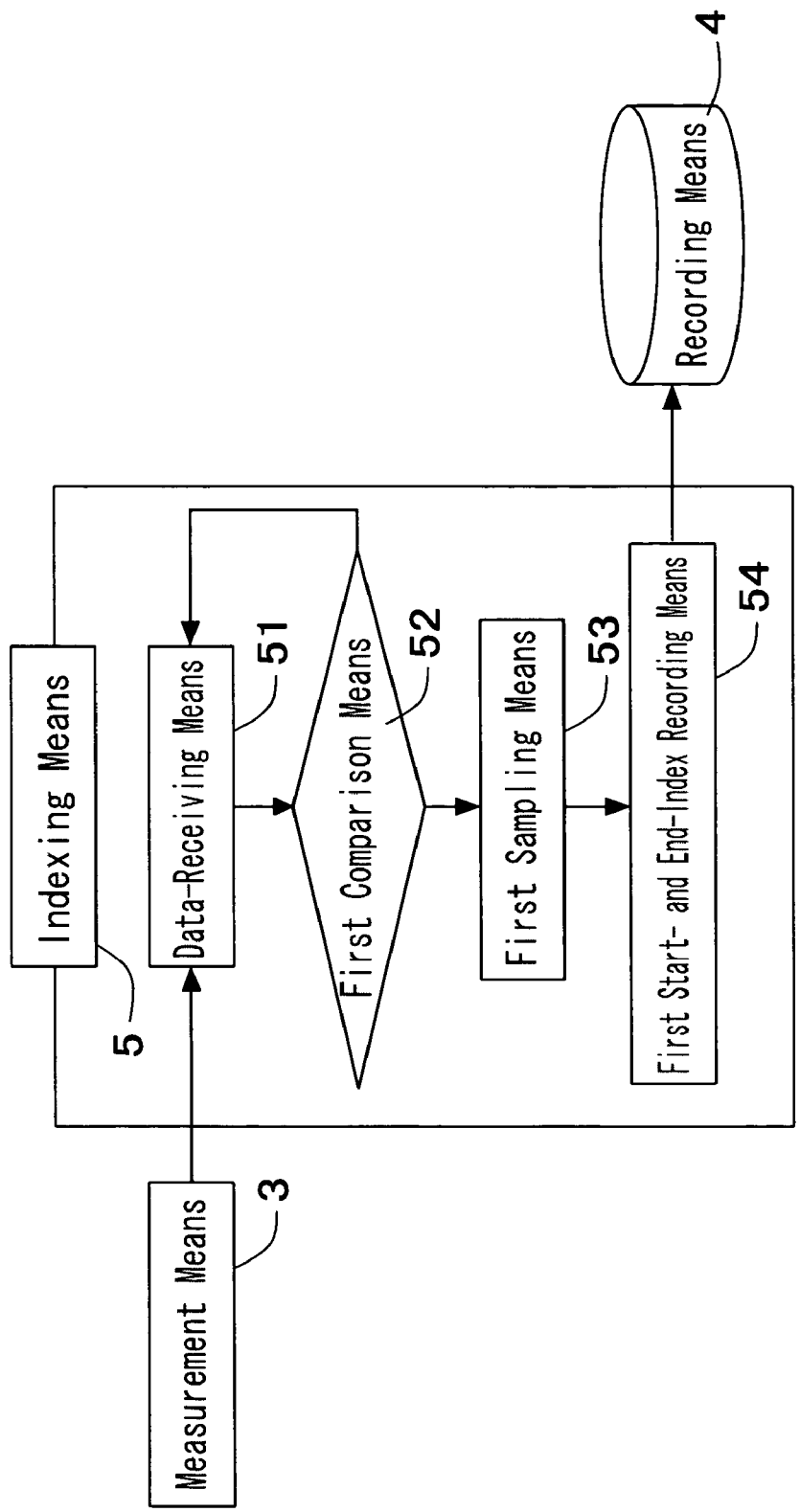
FIG. 3 is a block diagram illustrating the first indexing method.

The indexing means (5) configured to perform the first indexing method includes a data-receiving means (51), a first comparison means (52), a first sampling means (53), and a first start-and-end-index-recording means (receiver) (54) (See FIG. 3).

The data-receiving means (51) receives the physiological data from the measurement means (2) successively and in chronological order.

The first comparison means (comparator) (52) compares the physiological data received by the data-receiving means (51) with a predetermined threshold. The user may arbitrarily set any threshold and vary the set threshold depending on the physiological condition measured by the measurement means (3). The threshold is adjusted so that physiological data exceeding the threshold should indicate an unusual state. For example, for a surgeon having a usual heart rate of 60 beats per minute, the threshold may be set as 100 beats per minute. In this case, a heart rate more than 100 beats per minute is considered as an unusual state. The threshold may be set as a value (usual value+$\alpha$) that is slightly higher than the usual value. The usual value is previously calculated about the usual state of the surgeon in his daily life. Alternatively, the threshold may be equivalent to the physiological data obtained when the surgeon is in an unusual state.

If the physiological data exceeds the threshold, the first comparison means (52) allows for the first sampling means (53) (described below) to be activated. On the other hand, if the physiological data is below the threshold, the first comparison means (52) compares the next physiological data with the threshold.

If the first comparison means (52) detects that the physiological data is above the threshold, the first sampling means (53) samples still image information from the medical movie recorded in the recording means (4). First, the first comparison means (52) detects a physiological data that is above the threshold. At the same time, the first sampling means identifies the still image using the time information indicating the time when the physiological data exceeds the threshold. Once the still image is identified, the first sampling means (53) identifies still image information of this still image. The still image information includes, for example, the time information, index information, the address information, and the position information indicating where the still image is located in the medical movie. Although it is possible to sample the still images themselves, only the still image information is preferably sampled from the medical movie, considering the data volume of the still images and the fact that the medical movie which the still images belong to is recorded in the recording means (4).

The first start-and-end-index-recording means (54) records the still-image information sampled by the first sampling means (53) in the recording means (4) as start-index information of the medical movie. Further, if the first comparison means (52) detects that the physiological data is below the threshold after the first sampling means (53) samples the still-image information, the first start-and-end-index-recording means (54) enables the first sampling means (53) to sample still-image information from the medical movie recorded in the recording means (4). The first start-and-end-index-recording means (54) then records the still-images in the recording means (4) as end-index information of the medical movie. In this process, the still image information is sampled by the first start-and-end-index-recording means (54) from the still image of the moment when the physiological data falls below the threshold.

The first start-and-end-index-recording means (54) is designed to stay in the idling mode even if it receives an instruction to sample still-image information from the first comparison means (52), after the first sampling means (53) sampled still image information. Thus, the first sampling means (53) samples the still-image information of the moment when the physiological data exceeds or falls below the threshold (i.e. the moments when the chronological change curve intersects the threshold line).

Figure 4:
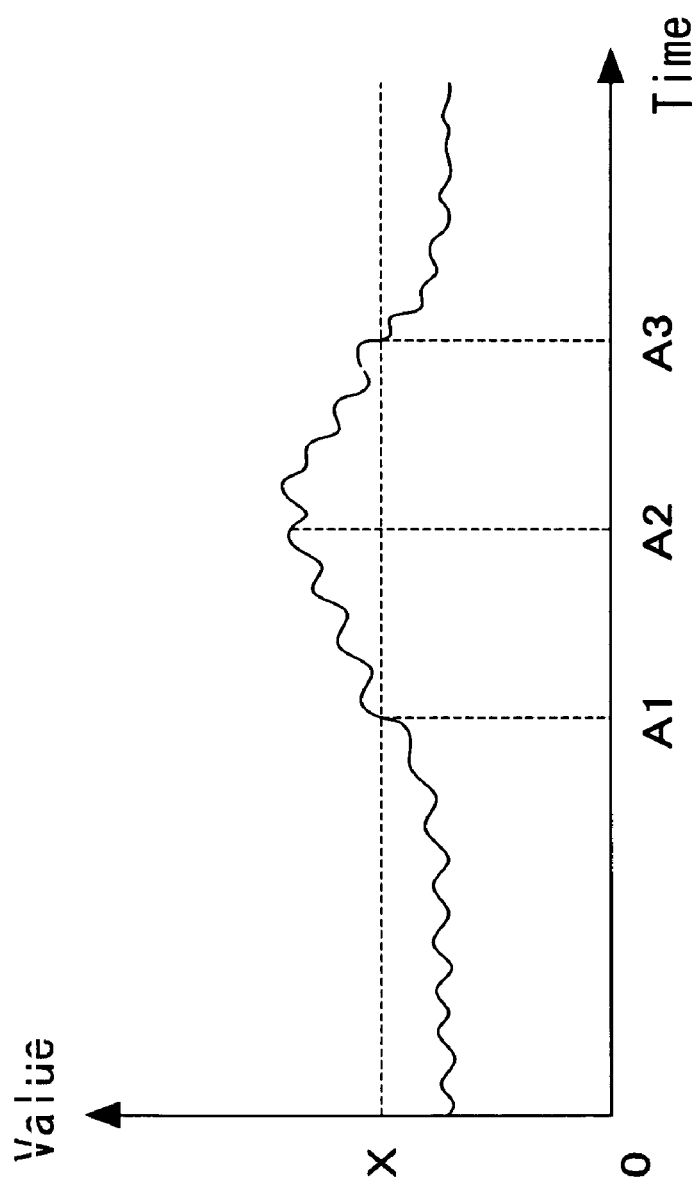
FIG. 4 is a graph showing the moment when the still-image information is sampled based on the physiological data.

For example, in the chronological change as shown in FIG. 4, the physiological data first exceeds the threshold (x) at the moment A1. At the moment A1, the first comparison means (52) sends the first sampling means (53) an instruction to sample still-image information. Thus the still-image information of the moment A1 is sampled. The first start-and-end-index-recording means (54) records the still-image information as the start-index information. Then, at the moment A2, the first comparison means (52) sends the first sampling means (53) an instruction to sample still-image information. Because the first sampling means (53) is in the idling mode, the first sampling means (53) ignores the instruction from the first comparison means (53). Then at the moment A3, the first comparison means (52) detects that the physiological data falls below the threshold (x) after the physiological data exceeds the threshold. The first comparison means (52) then urges the first sampling means (53) to sample still image information. The first start-and-end-index-recording means (54) records the still-image information sampled by the first sampling means (53) as the end-index information. During the time between the moments A1 to A3, the first sampling means is in the idling mode.

In this way, the still-image information sampled from the still image of the moment A1 is recorded as the start-index information while the still-image information sampled from the still image of the moment A3 is recorded as the end-index information. Therefore, the time between A1 to A3 is marked as an important scene in the surgery based on the physiological data of the surgeon.

Figure 5:
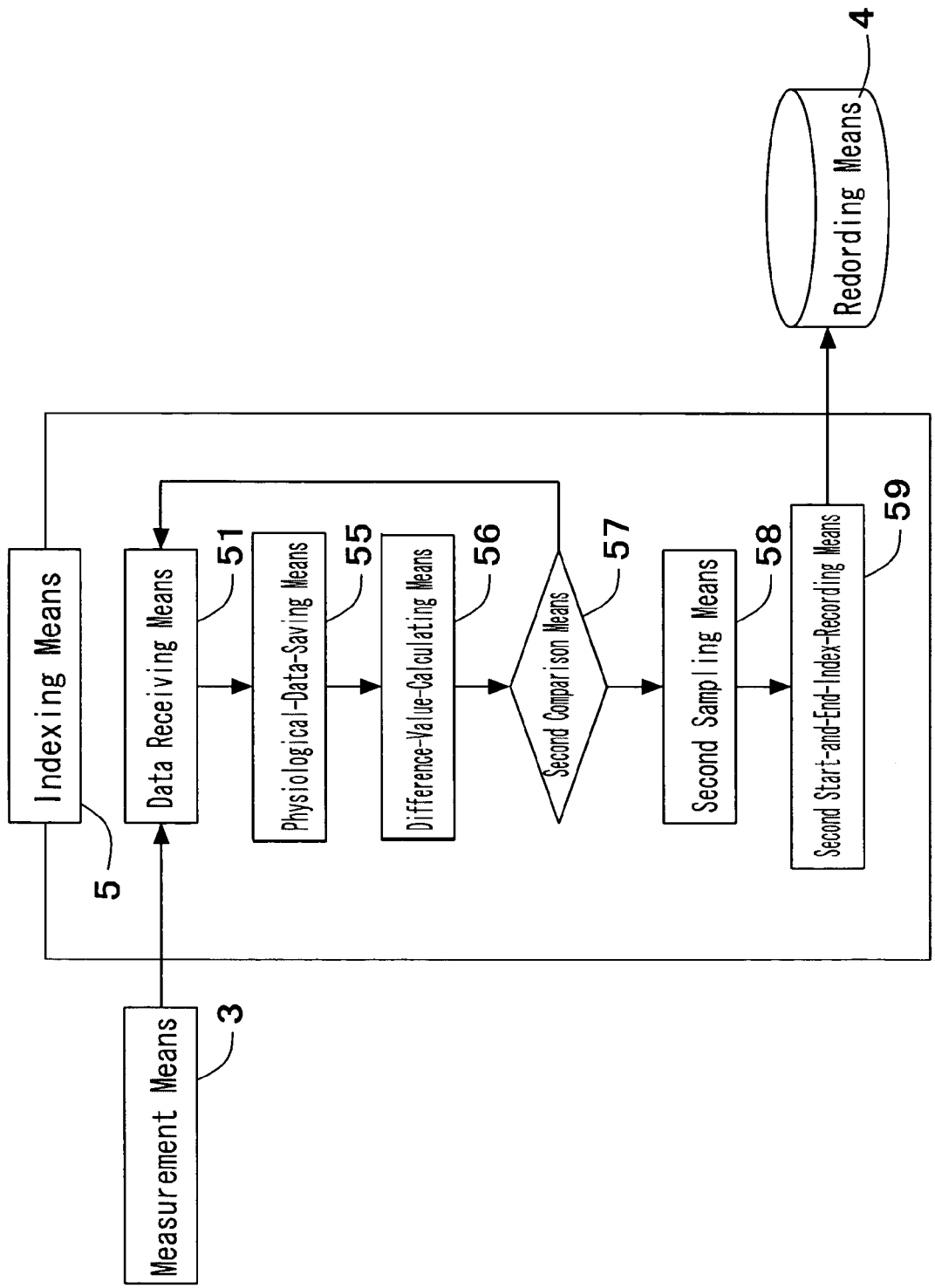
FIG. 5 is a block diagram illustrating the second indexing method.

Next, the second indexing method is explained (See FIG. 5).

The indexing means (5) configured to perform the second indexing method includes a data-receiving means (51), a physiological-data-saving means (55), a difference-value-calculating means (56), a second comparison means (57), a second sampling means (58), and a second start-and-end-index-recording means (59).

The data-receiving means (51) receives the physiological data obtained by the measurement means (3) as described above. The physiological-data-saving means (55) saves the chronologically ordered physiological data received by the data-receiving means (51). Common recording devices may be used as the physiological-data saving means (55). The physiological data are saved in the physiological-data-saving means (55) successively and in chronological order. The difference-value-calculating means (56) calculates the chronological difference-value between two adjacent physiological data saved in the physiological-data-saving means (55). The time interval between the two adjacent physiological data is preferably 0.1 to 0.2 seconds, and more preferably 0.01 to 0.02 seconds, but may be set as other intervals that are appropriate for calculating difference values useful for accurately estimating changes in the physiological data. The difference value calculated by the difference-value-calculating means (56) may be the average value of the two data. The second comparison means (57) compares the difference-value calculated by the difference-value-calculating means (56) with a predetermined threshold. The predetermined threshold may be, for example, the average value calculated for older set of data. In this way, the threshold and the physiological data are compared.

If the second comparison means (57) detects that the difference-value is above the predetermined threshold, the second sampling means (58) samples still-image information of the moment (referred to below as "first sampling moment") when the older physiological data of the two physiological data that are used to calculate the difference-value is measured. The second sampling means (58) samples still-image information from the medical movie in a basically similar manner to the first sampling means (53). The difference between the second sampling means (58) and the first sampling means (53) is that the second sampling means (58) samples the still-image information of the "first sampling moment".

The second start-and-end-index-recording means (59) records the still-image information sampled by the second sampling means (58) in the recording means (4) as the start-index information of the medical images.

On the other hand, if the second comparison means (57) detects that the difference value is below the threshold after the second sampling means (58) samples still-image information, the second start-and-end-index-recording means (59) samples still-image information of the moment ("second sampling moment") when the newer physiological data of the two physiological data that are used to calculate the difference value is measured The still-image information sampled by the second start-and-end-index-recording means (59) is then recorded in the recording means (4).

Figure 6:
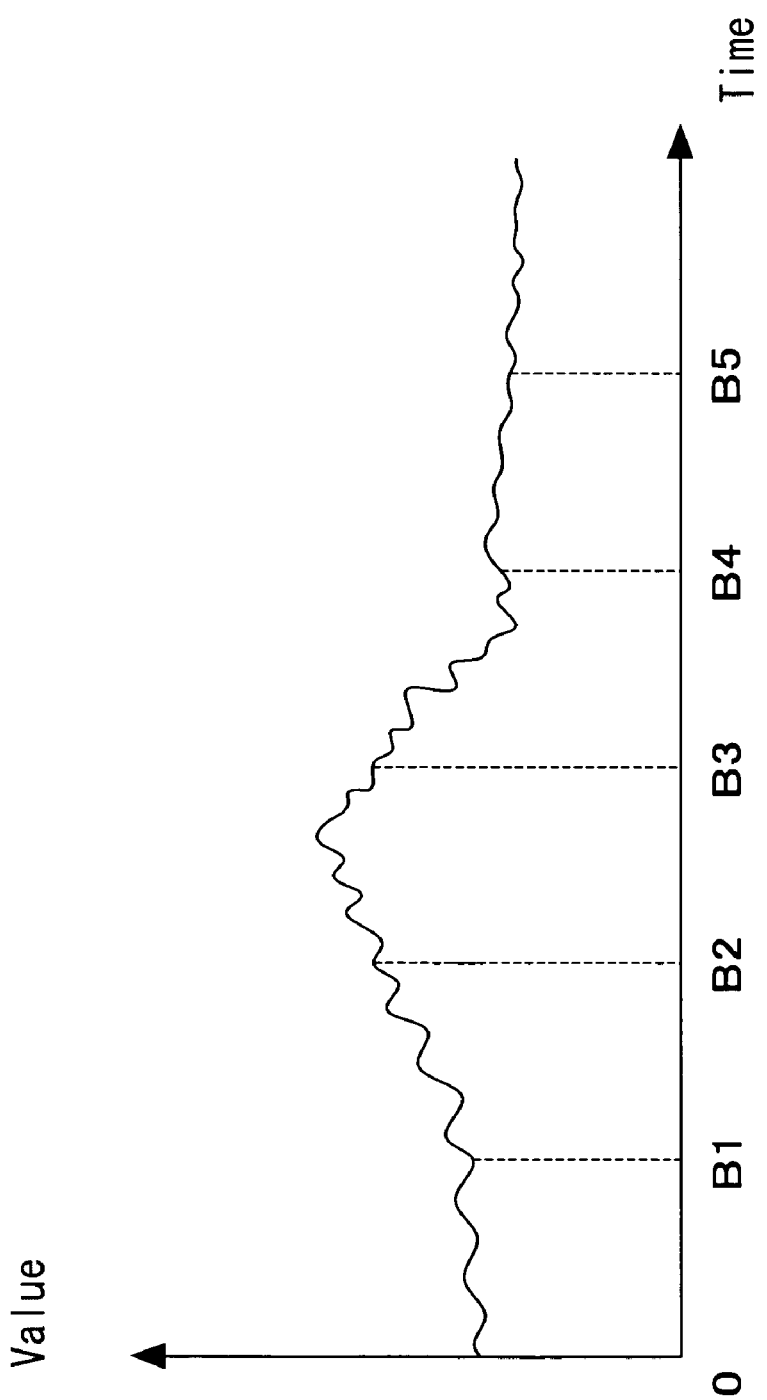
FIG. 6 is a graph showing the moment when the still-image information is sampled based on the physiological data.

The second start-and-end-index-recording means (59) adds the start-index information and the end-index information to the medical movies in a similar manner to the first start-and-end-index-recording means (54). The difference between the first and the second start-and-end-index-recording means (54) and (59) is that the second start-and-end-index-recording means (59) samples the still image information contained in the still image of the "first sampling moment" as the start-index information and the still image information contained in the still image of the "second sampling moment" as the end index information. For example, if the change as shown in FIG. 6 occurs in the physiological data graph, the data-receiving means (51) receives physiological data at each of the moment B1, B2, B3, B4, and B5, and sends the physiological data to the physiological-data-saving means (55). The physiological-data-saving means (55) records therein the physiological data sent from the data-receiving means (51) and sends the recorded data to the difference-value-calculating means (56). The difference-value-calculating means (56) calculates the difference value for each time interval defined by adjacent two of B1 to B5. Firstly, the average value of the physiological data between the moment B1 and the moment B2 is calculated. The average value is referred to as the first average value or the former average value.

Next, the difference-value-calculating means (56) calculates the average value of the physiological data between the moment B2 and the moment B3. The average value is referred to as the second average value or the latter average value. The second comparison means (57) compares the first average value and the second average value.

If the second average value is greater than the first average value and if the difference between the second and the first average value is greater than a predetermined threshold, the second sampling means (58) is urged to be activated. The threshold may be set by the user as any value. Also, the predetermined threshold may be adjusted depending on the type of the physiological data or the surgeon subjected to the physiological measurement.

The above-described process is repeated for each time interval. In the example shown, the second difference value between the moment B2 and the moment B3 is significantly different from the first difference value of the moment B1 and the moment B2. Therefore, the second sampling means (58) samples from the medical movie the still image information of the "first sampling moment". In this example, the still-image information at the moment B2 is sampled. The sampled still-image information is recorded in the recording means (4) as the start-index information.

Furthermore, the second start-and-end-index-recording means (59) obtains the end-index information. First, the difference-value-calculating means (56) calculates difference value (the third average value) between the moment B3 and the moment B4 as well as the difference value (the fourth average value) between the moment B4 and the moment B5. Then the second comparison means (57) compares the third average value and the fourth average value. Detecting a significant difference between these values, the second comparison means (57) sends the second sampling means (58) an instruction to sample still-image information. The still-image of the "second sampling moment" (the moment B4 in this example) is recorded in the recording means (4) as the end-index information. If the interval between B1 and B5 shown in FIG. 6 is shortened, it is possible to detect smaller changes in the physiological data, as well as to add a start-index and an end-index to the medical movie whenever these changes are detected.

The physiological data is saved in the physiological-data-saving means (55). In another embodiment, the physiological data previously saved in the physiological-data-saving means (55) may be used to calculate the start time and the end time of the changes in the physiological data. For example, if it is detected that one of the physiological data is above the predetermined threshold, the wave form of this physiological data is plotted (i.e. changes in this physiological data is monitored). Algorithms (e.g. genetic algorithm, neural network and fuzzy logic) for obtaining optimal solutions may be used to calculate the start time at which the physiological data start to deviate from the usual range and the end time at which the physiological data returns to the usual range. The data between the start time and the end time of one change is handled as one group of the physiological data. Among the groups of the physiological data saved in the physiological-data-saving means (55), a data group having unique characteristics is specified to detect changes in the physiological data.

In the first and second indexing method, an index-adjusting means (60) may be preferably used. The index-adjusting means (60) shifts back (with respect to the time vector) the start-index information by a predetermined time length and shifts forward the end-index information by a predetermined time length. Thus, when the user views the medical movie, the medical movie starts from the moment that is earlier than the start of a change in physiological data by a certain time length and ends at the moment that is later than the end of the change by a certain time length. The time length is not particularly limited but the user may choose any time length. If the start-index information and/or the end-index information are adjusted by the index-adjusting means (60), the adjusted index information is added to the medical movie and recorded in the recording means (4) together with the medical movie.

Figure 7:
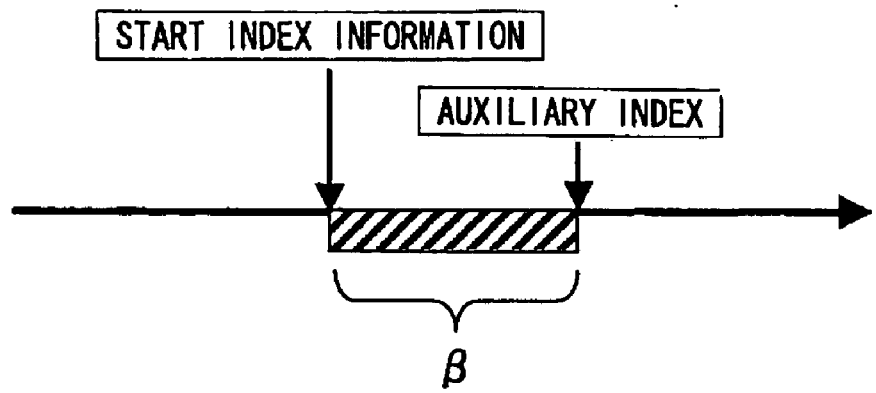
FIG. 7 is view illustrating the methods of using auxiliary indices to add index information to the medical movie.
Figure 7:
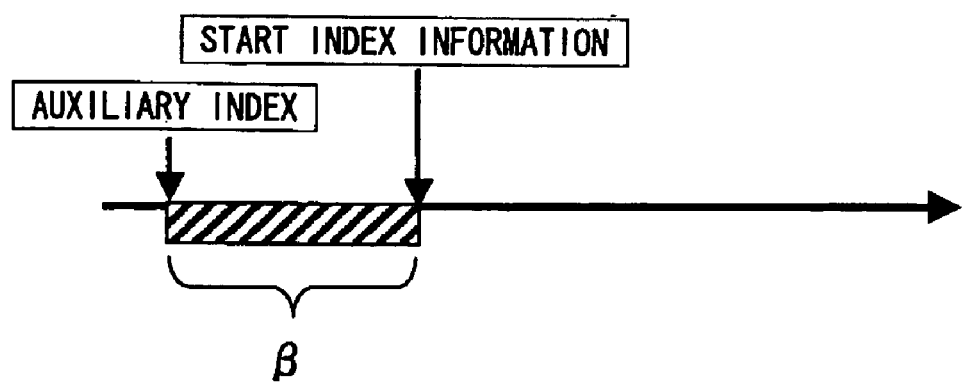
Figure 7:
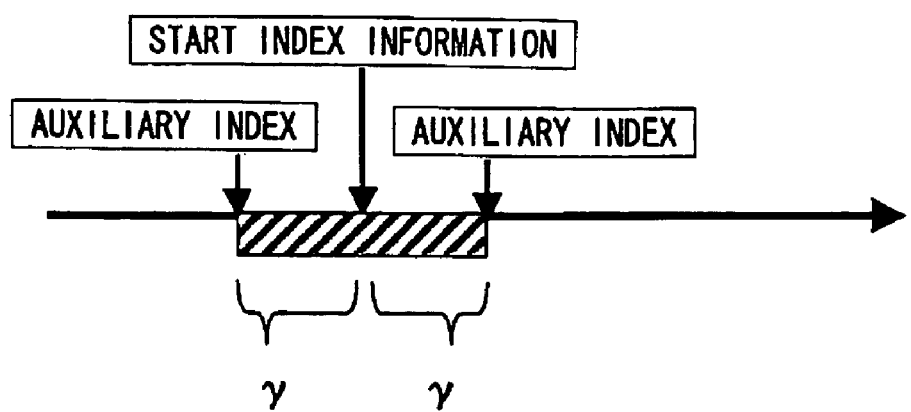

In another embodiment, still image information from a plurality of still images may be sampled as the start-index information and the end index information. Those still images from which the still image information is sampled include the still image of the moment when the comparison means (4) sends an instruction to sample still image information as well as several still images before and/or after that still image. In the examples described above, the index information is the still image information of one moment and the still image information indicates one moment. In the present example, the still image information is sampled from the still images corresponding to the time period that starts sometime before the moment when the index information is sampled and ends sometime after the moment when the index information is sampled. Therefore the index information in the present example samples a medical movie of an important scene continuing for a certain time length. For example, as shown in FIG. 7(a), an auxiliary index is set to the position that is later than the sampled start index by a duration β. All the still images between the start-index information and the auxiliary index are labeled as index information. In an example shown in FIG. 7(c), one auxiliary index is set to the position that is earlier than the sampled start-index information by a duration γ and another index is set to the position that is later than the sampled start-index information by the duration γ. All the still images between the two auxiliary indices (i.e. the medical movie between the two auxiliary indices) are labeled as index information. End-index information can be set in the same manner as the example shown in FIG. 7. The user may set the duration β and γ as any duration. FIG. 7(c) shows the example of the two auxiliary indices that are positioned symmetrically with respect to the start-index information but the auxiliary indices may not be necessarily positioned symmetrically. The index information that is sampled from a plurality of the still images may be recorded in the recording means (4).

The start-index information and the end-index information sampled by the first sampling means (53) and the second sampling means (58) may be used to sample the medical movie recorded between these index information. The still images between the start-index information and the end-index information may be sampled instead of the medical movie. In addition to sampling the medical movie and the still images between the start-index information and the end-index information, it is possible to sample the index information of the start- and the end-index information as well as to sample the index information, address information, time information of all the still images in the time duration. The sampled medical movie or still images, or their index information, address information, and the time information are displayed in the still image window described below.

Preferably, image property information is assigned to each of the sampled index information, the medical movie, and the still images. The image property information is helpful in a quick check on the property of the sampled information.

Preferably, a foot switch (foot-operated switch), a manual switch, a remote controller with manual buttons are available for the surgeon to add the above-described index information to the medical movie. Thus, it is possible to obtain the medical movies in either way, according to the surgeon's will or the physiological data.

Figure 8:
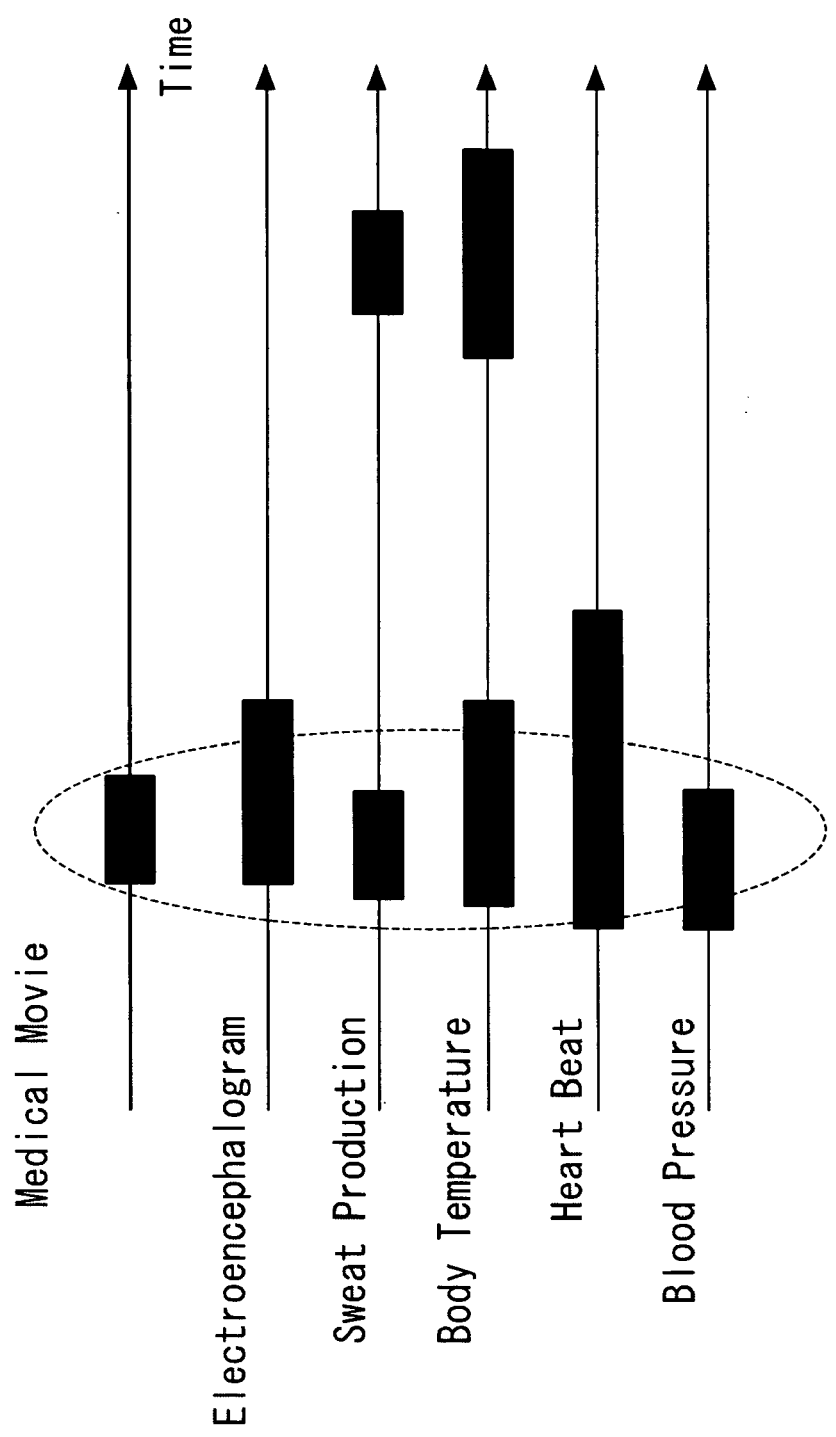
FIG. 8 is a graph showing the moment when the still-image information is sampled based on the physiological data.

As described above, medical image management system (1) is capable of adding the start-index information and the end-index information to the medical movie according to the changes in the physiological data. The physiological data includes at least one of physiological parameters selected from a group consisting of the surgeon's heart beat, blood pressure, sweat production, body temperature, electroencephalogram, grip strength, point of gaze, blink, pupil, eye movement, respiratory rate (including apneic period), pneumogram, number of swallowing, skin electric conductance, electric potential difference of muscle, neurotransmitter level, blood glucose level, blood flow rate, blood composition, amount of various hormones, chewing pressure, electrocardiogram, galvanic skin reflex, fingertip pulse wave, posture or position, tear production, tear composition, saliva production, saliva composition, gastric secretion, gastric fluid composition, facial expression (measurement in characteristic analysis), vocal change (measurement in characteristic analysis), lip reading (measurement in characteristic analysis), limb shivering, and urine (protein level, sugar level, occult blood level). In some examples as shown in FIG. 8, several types of index information are assigned to one medical movie. In these examples, each type of index information is compared with the predetermined threshold in order to more accurately sample a medical movie showing an important scene of the medical treatment. In the dotted area shown in FIG. 8, heart rate, blood pressure, sweat production, body temperature, and electroencephalogram simultaneously have an unusual value. This makes it possible to presume that the medical treatment in this scene is extremely stressful. The relative importance of the scenes constituting the medical treatment can be estimated by obtaining several different types of physiological data and calculating when these different types of physiological data simultaneously record an unusual value.

If data of grip strength is obtained among the physiological data, it is possible to record significant changes in grip strength in the medical movie as the index information. Checking the medical movie sampled by using such index information together with the changes in the grip strength data is helpful in understanding how instruments such as a surgical knife are used.

It is easy to sample a part of the medical movie that captures medical treatment such as skull drilling during a brain surgery by using the changes in grip strength because such medical treatment accompanies comparatively large hand motion and resultant significant changes in grip strength.

In surgeries (e.g. sclerotomy process during an ophthalmic operation using a microscope) that accompany smaller hand motion and resultant insignificant changes in grip strength, the changes in grip strength will not be a sufficient physiological data. In this case, electroencephalogram is used as physiological data in addition to grip strength. Electroencephalogram records muscle movement even in a hand motion that accompanies little change in grip strength. Data of grip strength and electroencephalogram as an auxiliary data cooperatively serve for accurate detection of changes in the physiological condition.

A surgeon with little experience in the medical treatment can study the important scenes in the medical treatment. This results in a effective simulation of the medical treatment so that the inexperienced surgeon can understand what scenes can be stressful before he actually performs the same treatment.

Figure 9:
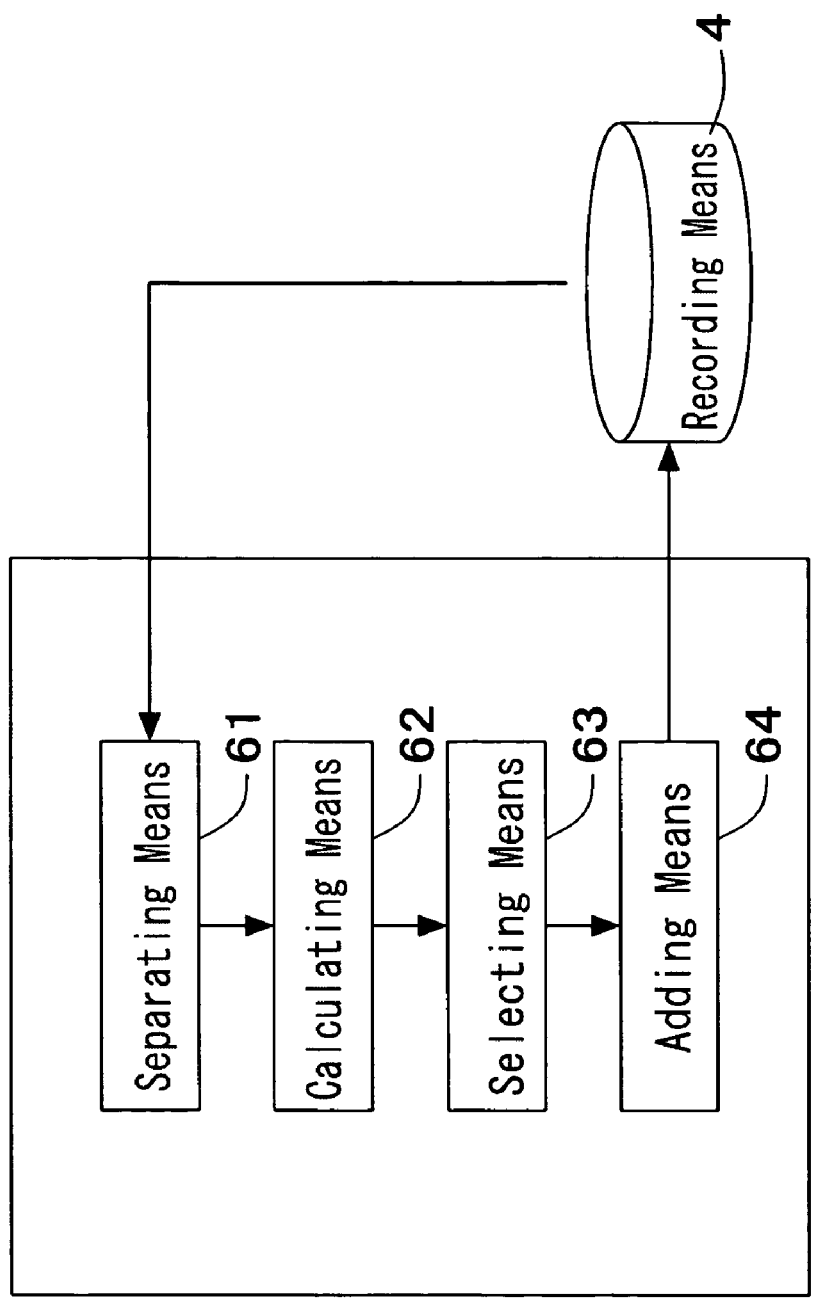
FIG. 9 is a block diagram illustrating the configuration for separating still images from the medical movie.

The medical image management system (1) further includes a separating means (61), a calculating means (62), a selecting means (63), and an adding means (64) configured to detect changes in the medical movie (See FIG. 9). The separating means (61) separates chronologically-ordered still images from the medical movie recorded in the recording means (4). The separating means (61) preferably separates still images from the medical movie at an interval of one frame, though the length of separating interval is not limited to this. Producing one still image per one frame is preferable considering the display device (described below) displays the medical movie frame by frame. In addition, still images produced for every one frame reveal extremely small changes in the medical movie.

The calculating means (62) calculates coordinate values in color space of each still image separated by the separating means (61). These coordinate values may be RGB (Red-Green-Blue) value, YUV (PAL-Phase Alternation by Line) value, YCbCr (ITU-R BT.601) value, and XYZ (CIE 1931) value and other values that are useful for detecting a difference in color of the still images.

The selecting means (63) compares the coordinate values in the color spaces of two chronologically adjacent still images. If the difference in the coordinate values in the color spaces of the adjacent two still images exceeds the predetermined threshold, the selecting means (63) selects these two still-images. In such comparison by the selecting means (63), first the still images contained in the medical movie are arranged in a chronological order and then chronologically adjacent still images are compared. A histogram obtained by calculating the coordinate values in the color spaces may be used in the comparison. If a set of coordinate values in color spaces results in a greater difference than a predetermined threshold, the selecting means (63) selects the still image having with this set of coordinate values. The threshold can be set to any value by a user.

Adding means (64) adds image-difference information to the still images selected by the selecting means (63). The image-difference information is added to the medical movie as the index information and recorded in the recording means (4) like the start-index information and the end-index information. In this way, when the still images are separated from the medical movie, coordinate values in the color space of the separated still images may be used to estimate the difference between the separated still images. The difference between the still images may be compared with the changes in the physiological data.

Figure 10:
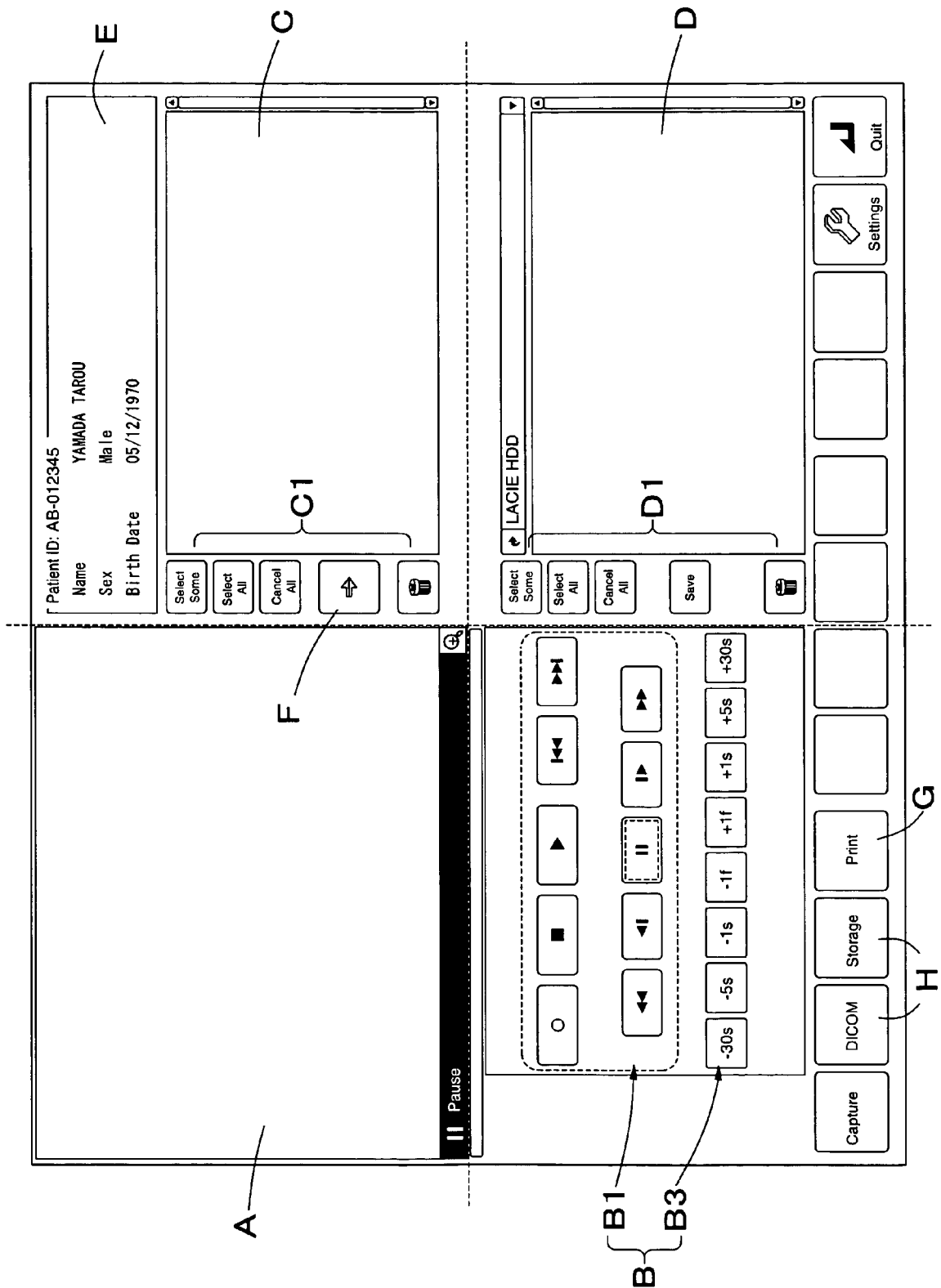
FIG. 10 is a view illustrating one embodiment of the display included in the output means.

The medical image management system (1) of the present invention further includes an output means (7). As shown in FIG. 10, the output means (7) includes a first display (A) and a second display (C). The first display (A) displays the medical movie captured by the medical imaging device (2). The second display (C) displays the still images from which the first and the second sampling means (53) and (58) sample the still-image information. The movie and the still images of the first display (A) and the second display (C) are displayed on the same screen. The output means (7) further includes an operating portion (B) and a movie display (D) configured to show the medical image saved in the recording means (4). The screen of the output device is divided into four sections and the four section has the first display (A), the operating portion (B), the second display (C), and the movie display (D), respectively. FIG. 10 shows the first display (A) in the upper left position, the operating portion (B) in the bottom left, the second display (C) in the upper right, and the movie display (D) in the bottom right but the arrangement of these is not limited to this. The arrangement shown in FIG. 10 is preferable to makes it easy to edit the movie on the screen. The resolution of the screen may preferably be ranged from 1024× 768 pixels to 1280×1024 pixels considering that all of the first display (A), the operating portion (B), the second display (C), and the movie display (D) are shown in the screen, but the resolution range is not limited to this. In the example of FIG. 10, above the second display (C) is the patient display (E) configured to display identification information of patients. A converting means (F) is arranged in the bottom of the screen.

The first display (A) shows and plays the medical movie and the still images recorded in the recording means (4). As the medical movie and the still images captured with the medical imaging device (2) are played on the first display (A), it preferably has the above-mentioned resolution and is capable of showing screen colors of more than 16 bits or 24 bits. The number of colors is not limited to these but can be selected according to the capacity of the medical imaging device (2).

Figure 11:
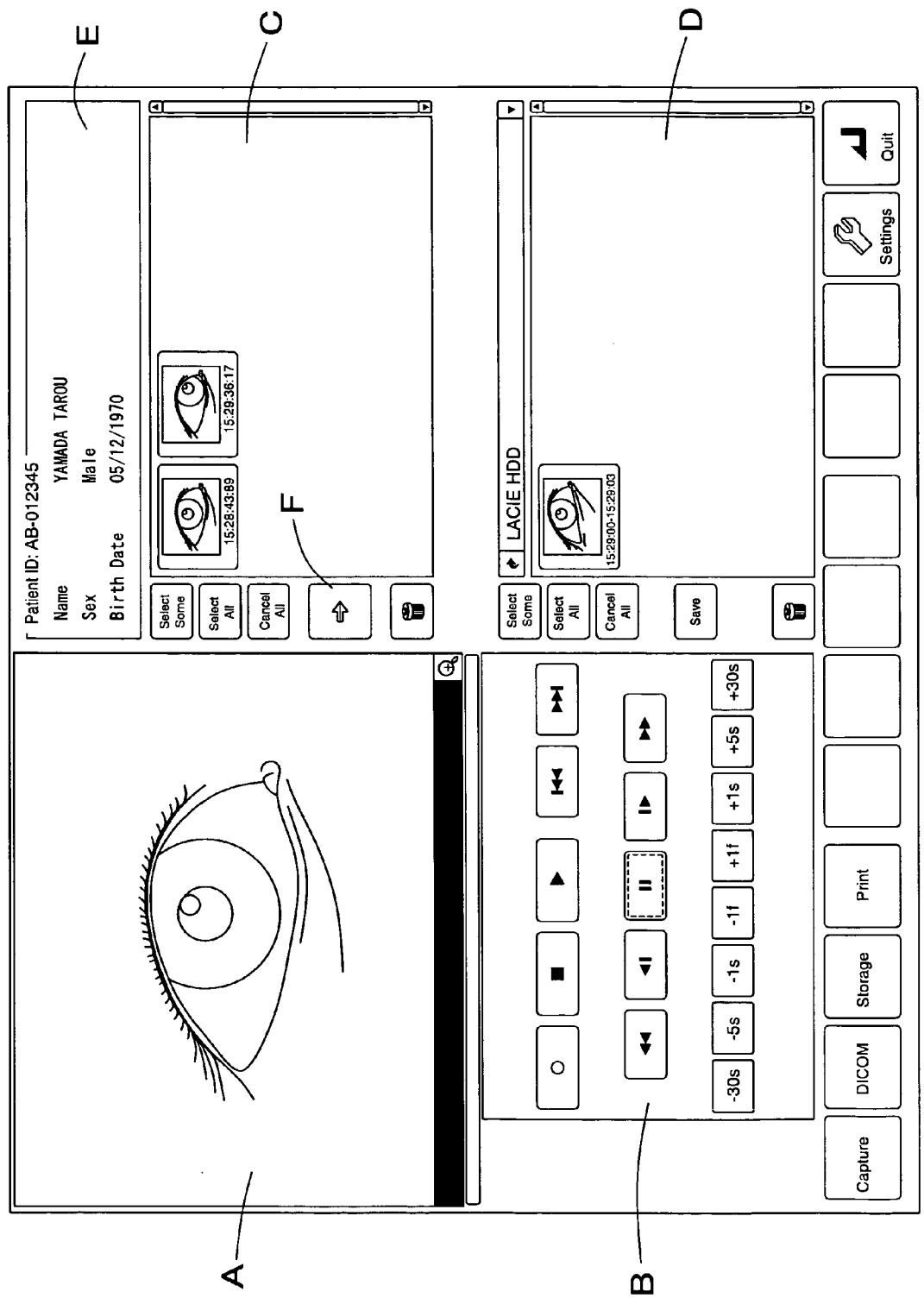
FIG. 11 is a view illustrating one embodiment of the display included in the output means.

In FIG. 11, the second display (D) (described below) shows a medical movie (medical movie file) that is recorded in the recording means (4) while the first display (A) shows the beginning of the movie.

The operating portion (B) is used to operate the movie shown in the first display (A). The operating portion (B) is shown in the screen to be directly pointed with a coordinate input device (e.g. a mouse). The operating portion enables operations such as play, stop, rewind, and fast forward, pause, play at fast speed, rewinding play, and switch to another movie (B1). The operating portion (B) facilitates viewing the medical movie. Preferably, the output means (7) further includes sampling portion (F) configured to sample a still image from the medical movie shown in the first display (A) by using the operating portion (B). The sampling portion (F) is pointed by a coordinate input device such as a mouse to sample a still image from the movie shown in the first display (A). In the figures (e.g. FIG. 11) of this embodiment, the sampling portion (F) is arranged between the first display (A) and the second display (C) because the still image is sampled from the movie shown in the first display and shown in the second display (C). However, the sampling portion (F) may be arranged in any position on the same screen of the output device (7) as the first display (A), the operating portion (B), and the second display (C). FIG. 11 shows a screen of the moment after sampling two still images from the movie files shown in the movie display (D). At this moment, the first display (A) shows one of the still images (the left image as shown in FIG. 11) listed in the second display (C). The second display (C) shows the still image with start-index information. If the still-image is selected, the first display runs a movie of the time duration from the time specified by the start-index information to the time specified by the nearest end-index information.

As shown in FIG. 10, the operating portion (B) includes an auxiliary operating portion (B3) for forwarding or rewinding the movie played (or displayed) in the first display (A) by a predetermined time length. The auxiliary operating portion (B3) is capable of forwarding or rewinding the movie in the first display (A) by a predetermined time length and playing the movie after the forwarding or the rewinding in the first display (A). The auxiliary operating portion (B3) shown in FIG. 10 is capable of forwarding and rewinding by 30 seconds, 15 seconds, one second, and one frame, but the time length is not limited to these. Shorter frame interval is preferable but the user can set any frame interval. If the auxiliary operating portion (B3) is used, the first display shows a still image of a moment some time before/after the moment of the scene previously shown in the still image on the first display (A). If the function "rewinding for one second" is used while playing the movie of the time 1:30, the first display (A) shows the movie (still image) corresponding to the time 1:29. By accurately selecting the time of the movie or the still image to play in the display (A) in this way, desired movie or still image is played in the first display (A).

The second display (C) shows the still image to which the indexing means (5) added index information or the first still image contained in a sampled medical movie. The still image shown in the second display (C) includes information about the medical movie from which the still image is sampled. The information of the original movie may include information for linking the still image to the original movie. As the still images shown in the second display (C) includes the information about the original movie, the first display (A) shows the corresponding still image contained in the original movie, if the still image shown in the second display (C) is selected with an appropriate coordinate input device. The second display (C) also lists the still image obtained while playing the movie in the first display (A). The second display further includes a still-image-operating-portion (C1) configured to handle the still images listed in the second display (C).

The movie display (D) shows the list of the movies recorded in the recording means (4) and of the sampled movie obtained according to the index information added by the indexing means (5). The list shown in the movie display (D) includes index information. Preferably, thumbnail-sized images or otherwise reduced images of the first still images of the movies are displayed in the movie display (D) to facilitate checking the content of each movie. However, the list of the movies may be displayed in other ways. The list shown in the movie display (D) may further include the playing time of each movie.

In the example of FIG. 10, the movie display (D) includes a movie editing portion (D1) configured to make a selection on the movies (or the movie files) listed in the movie display (D) and to edit the movies. The movie editing portion (D1) enables selecting or deleting some of the movies from the listed movies.

The patient display (E) shows the identification information of the patient appearing in the movie or the still image shown in the first display (A). The identification information may include, though not limited to these, the patient's name, sex, and birth date. If it causes a privacy problem to show such information, the patient display (E) shows no information.

Figure 12:
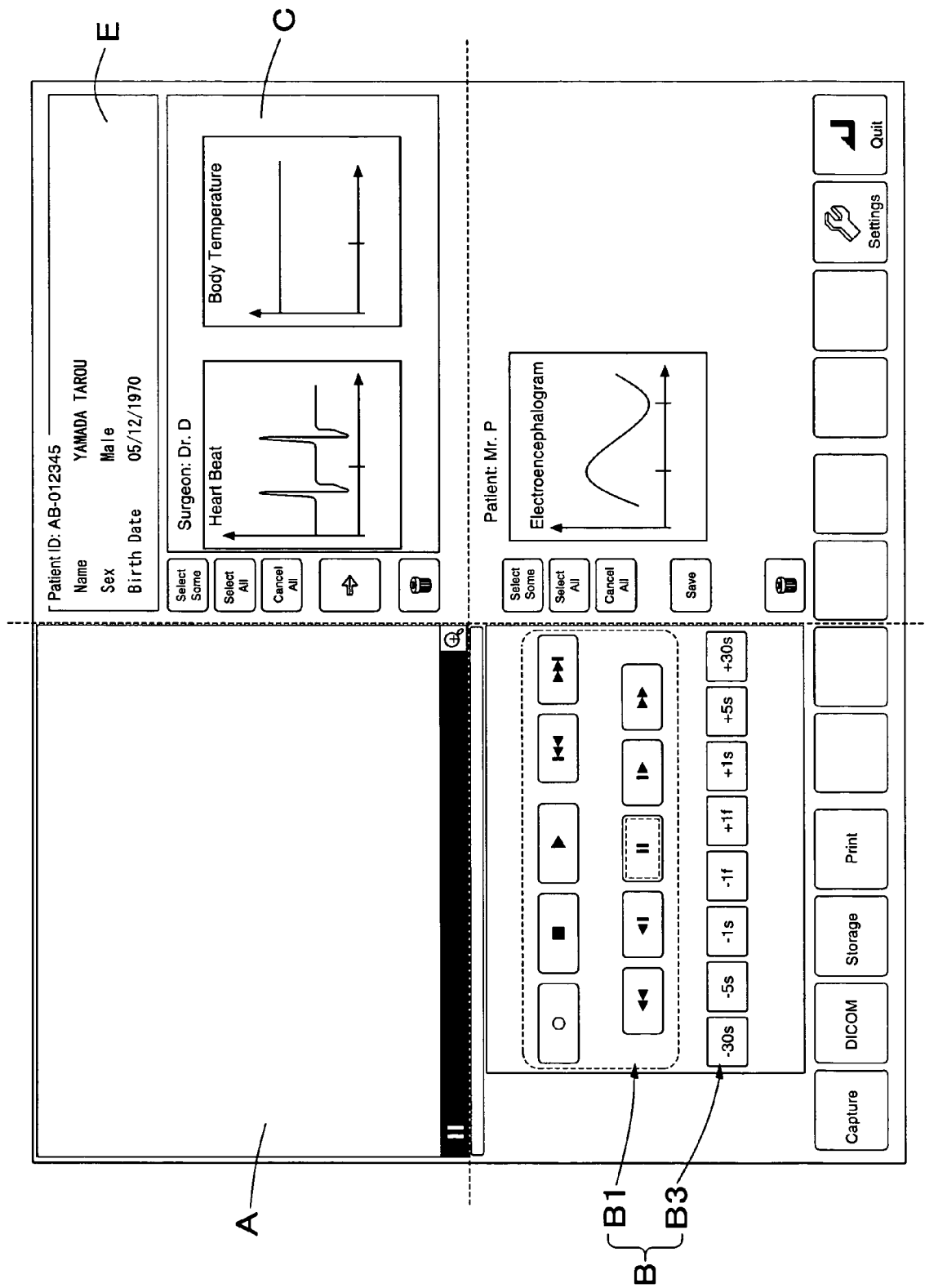
FIG. 12 is a view illustrating one embodiment of the display included in the output means. The display shows a graph of physiological data.

As shown in FIG. 10, the output means (7) may include a printing means (G) configured to output a selected still image to a printer that prints out the still image. The output means (7) may further include a converting means (H) configured to convert the still images (still image files) or the movies (movie files) listed in the second display (C) and the movie display (D) to a given image format. The converting means (H) may convert the movies to common image formats, such as DICOM (Digital Imaging and Communications in Medicine) and JPEG (Joint Photographic Experts Group). The converting means (H) separately includes a DICOM converting means and other converting means (storage converting means). As shown in FIG. 12, the output means (7) preferably shows graphs representing the changes in the physiological data synchronously measured with the medical movie shown in the first display (A). If the medical movie and the changes in the physiological data are synchronously displayed, it is possible to review the changes in the physiological data as the medical treatment progresses.

The output means (7) preferably shows a graph as shown in FIG. 8. For each physiological parameter, the graph shows the moment when the start-index information and the end-index information are added to the medical movie while the medical movie is recorded. While viewing the screen that simultaneously shows the medical movie and the corresponding physiological data, the user can review the important scenes in the medical treatment.

Preferably, the output means (7) further shows information measured or obtained by medical devices in a graph showing the chronological changes in the information. The information from the medical devices is preferably displayed synchronously with the medical movie by the output means (7). Thus the output means (7) synchronously displays the medical movie, the information from the medical devices, the changes in the physiological data obtained from the surgeon and/or the patients. Such display of the output means (7) enables the user to easily understand accurate chronological changes.

The configuration and the operation of the medical image management system (1) have been described above. Next, the medical image management method of the present invention will be described below.

In the medical image management system of the present invention, indices are added to important scenes occurring in the medical movie that is captured by the medical imaging device (2) according to the changes in the physiological data of the surgeon and the patient during the medical treatment. After the medical treatment finishes, the indices are used to facilitate viewing the important scenes occurring in the medical treatment.

Figure 13:
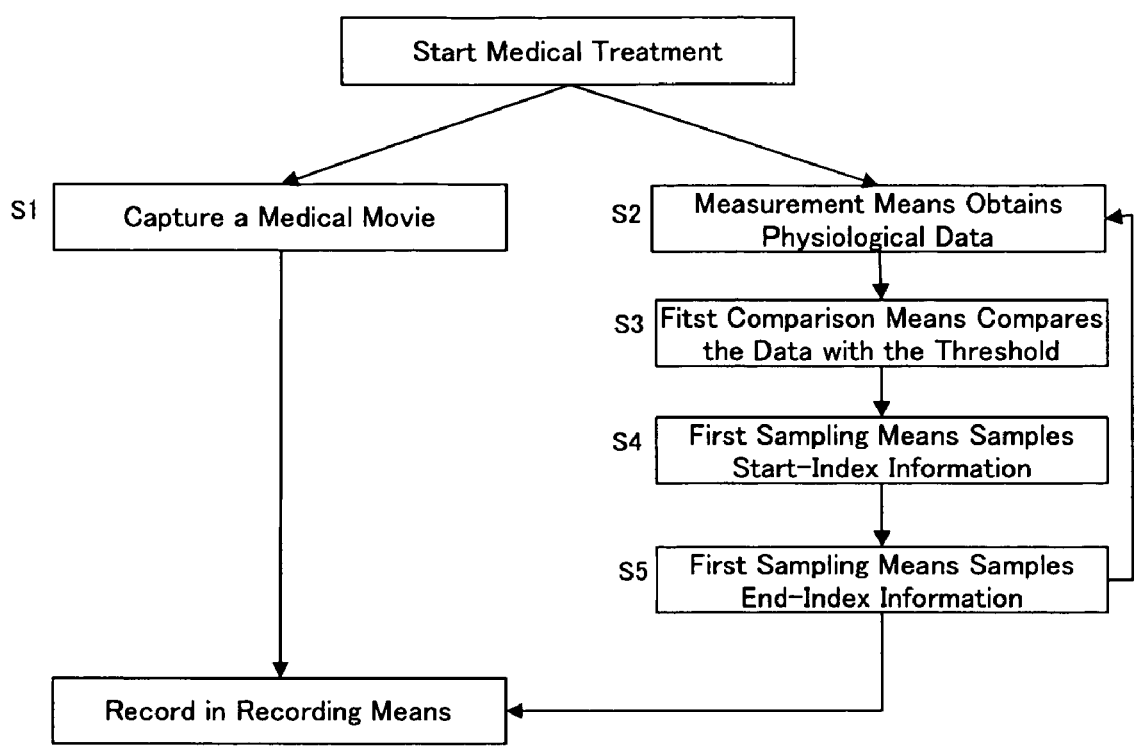
FIG. 13 is a flowchart illustrating the first indexing method.

FIG. 13 shows a flow chart representing the first indexing method. The medical imaging device (2) captures a medical movie showing the medical treatment (S1). At the same time, the measurement means (3) measures the physiological condition of the surgeon and the patient to obtain their physiological data (S2). If the first indexing method is used, the data-receiving means (51) receives the physiological data, and the first comparison means (52) compares the physiological data with the predetermined threshold (S3). When the comparison means (52) detects that the physiological data is above the threshold, the first sampling means (53) samples still image information from the medical movie as the start-index information (S4). The still-image information is sampled from the still image of the moment when the physiological data exceeds the threshold. When the physiological data falls below the threshold again, the first sampling means (53) samples still image information from the medical movie as the end-index information (S5). The still-image information is sampled from the still image of the moment when the physiological data falls below the threshold. The steps (S2) to (S5) repeat during the medical treatment. The index information is generated for each physiological data obtained. The index information is added to the medical movie and recorded in the recording means (4) (S6).

Figure 14:
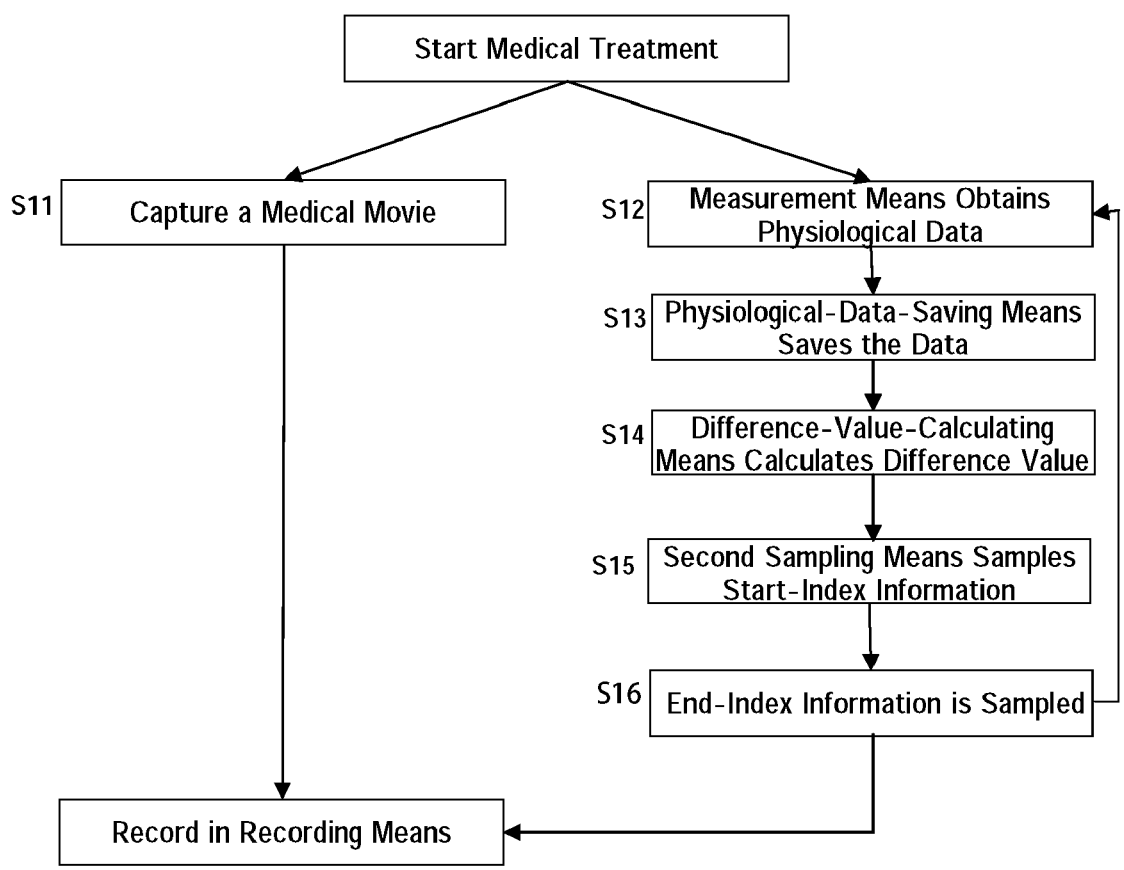
FIG. 14 is a flowchart illustrating the second indexing method.

As shown in FIG. 14, if the second indexing method is used, the medical imaging device (2) captures a medical movie (S11) and the measurement means (2) obtains physiological data (S12).

The data receiving means (51) receives the measured physiological data and the physiological-data-saving means (55) saves the physiological data in chronological order (S13).

Using the chronologically ordered physiological data saved in the physiological-data-saving means (55), the difference-value-calculating means (56) calculates the difference value at a predetermined time interval (S14).

When the second comparison means (57) detects that the calculated difference value exceeds the threshold difference value, the second sampling means (58) samples still image information as the start-index information (S15). The still-image information is sampled from the still image of the moment when the calculated difference value exceeds the threshold difference value. The still image information may be sampled from a plurality of still images as the start-index information.

When the difference value falls down the threshold difference value again, the second sampling means (58) samples still image information as the end-index information (S16). The still-image information is sampled from the still image of the moment when the calculated difference value falls down the threshold difference value. The still image information may be sampled from a plurality of still images as the end-index information.

The processes (S12) to (S16) repeat during the medical treatment. The index information is generated for each physiological data obtained. The index information is added to the medical movie and recorded in the recording means (4).

In another embodiment, the index-adjusting means (60) may be used to shift back/forward the start-/end-index information.

In yet another embodiment, the medical movie existing between the start-index information and the end-index information may be saved as a separate movie file in the recording means (4). The medical movie may be saved as a group of the still images in the recording means (4). In this embodiment, the second display (C) and the movie display (D) show the oldest still image contained in the sampled medical movie or in the group of the still images.

While the medical movie is saved in the recording means (4), information about the medical treatment and other events occurring in the medical treatment room is recorded, in addition to the start- and end-index information described above. Such information about the events during the medical treatment is helpful for more accurate estimate of the changes that occur during the medical treatment.

The information about the events during the medical treatment includes, for example, information about the time when a medical process is carried out, information about when medicines are administered, the information about verbal instructions given by the surgeon, signals from medical devices such as various types of physiological monitors that measure physiological conditions, information when medical personnel (including the surgeon) enter or leave the medical treatment room, information about operation of various devices and the like. Such information is recorded in the medical movie. For example, information about when "the surgeon A sprayed 50 mL of physiological saline around the incision site" is added to the medical movie as the index information.

The time information related to the surgeon and the medical personnel as well as medicines and various devices may be managed by attaching radio IC tags and codes (e.g. barcodes and QR codes) to these persons, medicines and devices respectively.

Figure 15:
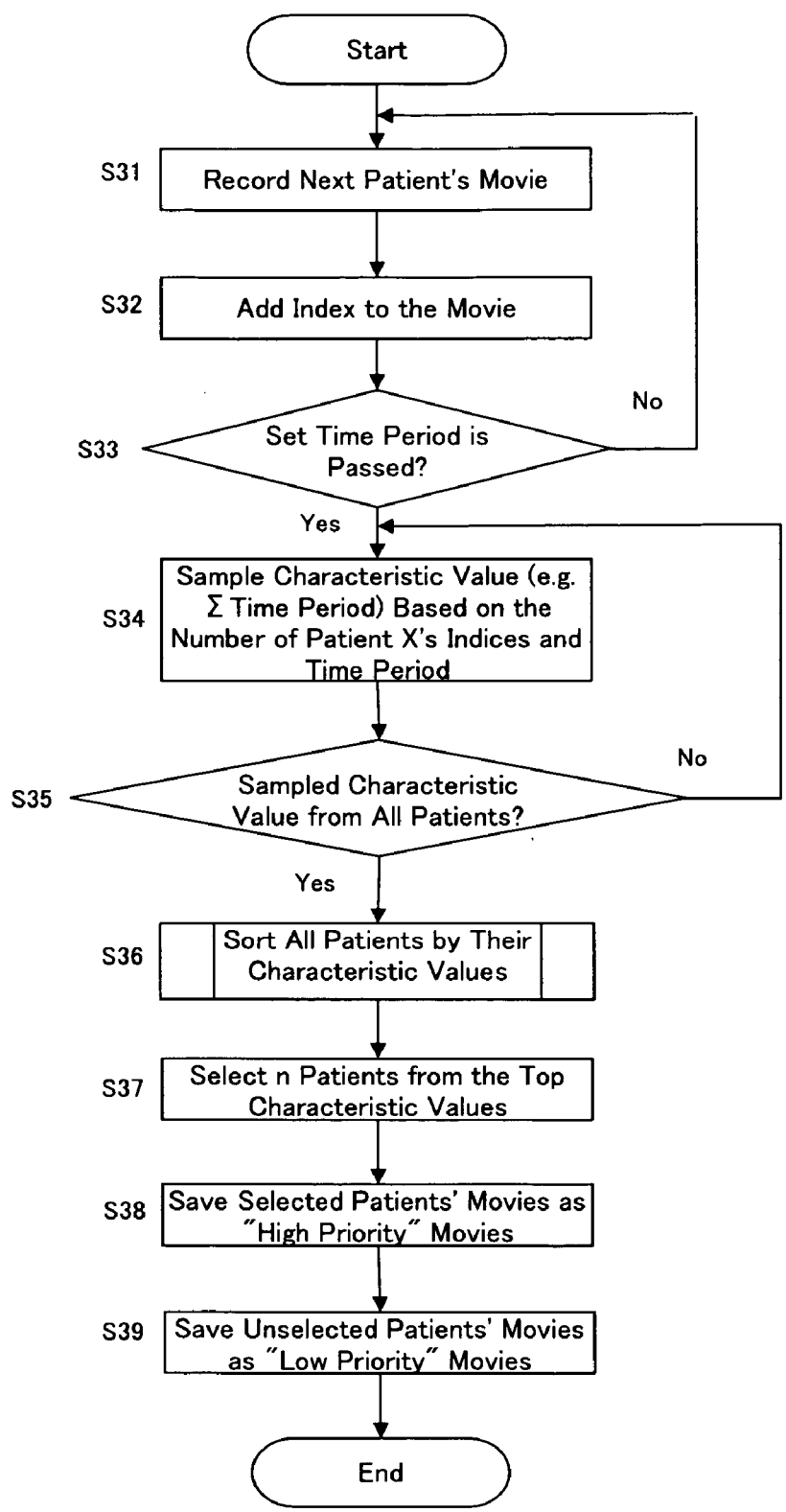
FIG. 15 is a flowchart illustrating the method of managing medical movies.

In another embodiment, the medical image management system (1) can be used for recording medical movies of a plurality of patients and effectively managing a plurality of the medical movies. FIG. 15 shows a flowchart representing one example of methods of managing a plurality of the medical movies.

First, several medical movies are saved for a certain time period. The time period may be one day, one week, one month, or any other term set by the user.

The medical movies of patients are recorded (S31). The index information is added to the medical movies using the medical image management system (1) while the movies are recorded (S32).

If the set time period is passed, the recorded medical movies are edited. If the set time period is not yet passed, more medical movies are captured (S33).

After the above-mentioned time period, the recorded movies are edited. Specifically, using the start-index information and the end-index information that are added to the medical movies according to changes in the physiological data, the time defined between each set of start- and end-index information is summed (S34). The longer the summed time (characteristic value: value showing characteristics of the movie) a movie has, the more important it is considered to be.

The step S33 is performed for every recorded medical movie of patients (S35). In this step, the characteristic value of all the medical movies is calculated.

Once the characteristic value of the medical movies of patients is obtained, the characteristic value is processed in the following steps. The characteristic value of the medical movies is saved in the recording means (4) (S36). Then the medical movies having a characteristic value that is above a predetermined threshold are selected from the medical movies (S37). The medical movies with higher characteristic value are selected. The threshold characteristic value may be set to any value by the user.

The selected medical movies are marked as "high priority" medical movies among others (S38). The "high priority" medical movies are subjected to processes enabling long-term storage. Such processes include, for example, lossless compression and compression with a low compression rate. Alternatively, the "high priority" medical movies may be kept uncompressed for a certain period.

The medical movies that remain unselected are saved as "low priority" medical movies (S39). The "low priority" medical movies are subjected to processes that enable storage for a shorter term than "high priority" medical movies.

In calculating the characteristic value, the time defined between a pair of index information may be variously weighted based on the importance of the physiological data for which the index information is generated. For example, the time defined between the indices generated for an important physiological data is multiplied by a comparatively large factor while the time defined between the indices generated for a less important physiological data is multiplied by a comparatively small factor. The characteristic value calculated in this way may be used to analyze brief surgeries, technically easy surgeries, and surgeries easily done by an experienced surgeon.

The preferred embodiments of the medical image management method using the medical image management system of the present invention have been described above.

Still image information is sampled from a medical movie based on the physiological data obtained from a surgeon during medical treatment. The sampled still image information indicates important scenes of the medical treatment including the scenes the surgeon is not aware of. The still image information may also be used for classifying medical movies according to their level of importance.

What is claimed is:

1. A medical image management system comprising:
   a medical imaging device configured to capture a medical movie of a patient who receives medical treatment, said medical movie consisting of a plurality of still images;
   a recording unit configured to record said movie captured with said medical imaging device;
   a measurement unit configured to measure physiological conditions of a surgeon who performs medical treatment on said patient and to obtain physiological data; and
   an indexing unit configured to add indices to said medical movie recorded by said recording unit according to said physiological data obtained by the measurement unit; and wherein
   said indexing unit includes
      a data receiving unit configured to receive said physiological data from said measurement unit,
      a comparison unit configured to compare said physiological data received by said data receiving unit with a predetermined threshold, and
      a first sampling unit configured to sample still-image information from said movie if said first comparison unit detects that said physiological data exceeds said threshold; and
   said still-image information is sampled by said first sampling unit from a still image of the moment when the physiological data exceeds said threshold.

2. The medical image management system of claim 1, wherein:
   said indexing unit further comprises a first start-and-end-index-recording unit configured to record said still-image information sampled by said first sampling unit as start-index information of said medical movie in said recording unit;
   if said first comparison unit detects that said physiological data falls below said threshold after said first sampling unit samples said still-image information, said first start-and-end-index-recording unit samples still-image information from said medical movie recorded in said recording unit and records said still-image information as end-index information of said medical movie in said recording unit; and
   said still-image information is sampled by said first start-and-end-index-recording unit from a still image of the moment when said physiological data falls below said threshold.

3. The medical image management system of claim 1, wherein said indexing unit includes:
   a physiological-data-saving unit configured to save said physiological data received by said data receiving unit in chronological order;
   a difference-value-calculating unit configured to calculate a chronological difference-value based on two adjacent said physiological data saved in said physiological-data-saving unit;
   a second comparison unit configured to compare said difference-value calculated by said difference-value-calculating unit with a predetermined difference-value; and
   a second sampling unit configured to sample still-image information from said medical movie if said second comparison unit detects that said calculated difference-value exceeds said predetermined difference-value; and
   wherein said still-image information is sampled by said second sampling unit from a still image of the moment when the older physiological data of said adjacent two of physiological data that are used to calculate said difference-value.

4. The medical image management system of claim 3, wherein:
   said indexing unit further comprises a second start-and-end-index-recording unit configured to record said still-image information sampled by said second sampling unit as start-index information of said medical movie in said recording unit;
   if said second comparison unit detects that said physiological data falls below said threshold after said second sampling unit samples said still-image information, said second start-and-end-index-recording unit samples still-image information from said medical movie recorded in said recording unit and records said still-image information as end-index-information of said medical movie in said recording unit; and
   said still-image information is sampled by said second start-and-end-index-recording unit from a still image of the moment when said physiological data falls below said threshold.

5. The medical image management system of claim 2 further comprising an index-adjusting unit configured to shift back said start-index information by a predetermined time length and to shift forward said end-index information by a predetermined time length.

6. The medical image management system of claim 4 further comprising an index-adjusting unit configured to shift back said start-index information by a predetermined time length and to shift forward said end-index information by a predetermined time length.

7. The medical image management system of claim 2, wherein said still-image information to be recorded as said start-index information and/or said end-index information is continuously sampled for a predetermined time length before and/or after said first sampling unit and said second sampling unit samples said still-image information.

8. The medical image management system of claim 4, wherein said still-image information to be recorded as said start-index information and/or said end-index information is continuously sampled for a predetermined time length before and/or after said first sampling unit and said second sampling unit samples said still-image information.

9. The medical image management system of claim 2, wherein said medical movie and/or said still-images is/are saved in said recording unit from when said start-index information is sampled and recorded in said recording unit to when said end-index information is sampled and recorded in said recording unit.

10. The medical image management system of claim 4, wherein said medical movie and/or said still-images is/are saved in said recording unit from when said start-index information is sampled and recorded in said recording unit to when said end-index information is sampled and recorded in said recording unit.

11. The medical image management system of claim 1 further including:
a separating unit configured to separate a plurality of chronologically-ordered still images from said medical movie recorded in said recording unit;
a calculating unit configured to calculate coordinate values in a color space of each still image that is separated by said separating unit;
a selecting unit configured to select two adjacent ones of said still images if the difference between the coordinate values of the two still images exceeds a predetermined threshold; and
an adding unit configured to add image difference information to each of said still images selected by said selecting unit.

12. The medical image management system of claim 1, further comprising an output unit, said output unit including:
a first display configured to display said medical movie captured with said medical imaging device; and
a second display configured to display said still images sampled by said first sampling unit and said second sampling unit.

13. The medical image management system of claim 1, wherein said measurement unit is configured to measure at least one physiological parameter selected from a group consisting of said surgeon's heart beat, blood pressure, sweat production, body temperature, electroencephalogram, grip strength, point of gaze, blink, pupil, eye movement, respiratory rate (including apneic period), pneumogram, number of swallowing, skin electric conductance, electric potential difference of muscle, neurotransmitter level, blood glucose level, blood flow rate, blood composition, amount of various hormones, chewing pressure, electrocardiogram, galvanic skin reflex, fingertip pulse wave, posture or position, tear production, tear composition, saliva production, saliva composition, gastric secretion, gastric fluid composition, facial expression (measurement in characteristic analysis), vocal change (measurement in characteristic analysis), lip reading (measurement in characteristic analysis), limb shivering, and urine (protein level, sugar level, occult blood level).

14. The medical image management system of claim 1, wherein all of said physiological data obtained by said measurement unit is recorded in said recording unit together with said medical movie that chronologically corresponds to said physiological data.

15. The medical image management system of claim 1 further configured to select movies to which a larger number of said indices are added from said plurality of medical movies recorded in said recording unit, and to carry out a predetermined process on said selected medical movies.

16. The medical image management system of claim 1, further including a manual indexing unit configured to enable said surgeon to add indices to said medical movies.

17. The medical image management system of claim 1, wherein said measurement unit is configured to measure grip strength or an electroencephalogram of said surgeon.

18. The medical image management system of claim 17, wherein measurement of said grip strength or said electroencephalogram occurs during a craniotomy.

19. The medical image management system of claim 17, wherein measurement of said grip strength or said electroencephalogram occurs during an ophthalmic surgery using a microscope.

20. A medical image management method of producing a medical movie of a patient who receives medical treatment and of managing said medical movie, the method including steps of:
recording said medical movies while obtaining physiological data of a surgeon; and
adding indices to said medical movie according to said physiological data of said surgeon.

21. The medical image management method of claim 20, wherein said indices are added to said medical movies according to a comparison between said obtained physiological data and a threshold or according to a chronological change in said obtained physiological data.

22. The medical image management method of claim 20, wherein said step of adding indices includes a step of sampling still-image information of still images contained in said medical movie.

23. The medical movie management method of claim 20, further including steps of:
calculating the moments to start sampling and to stop sampling said medical movie based on two of said sampled still-image information; and
sampling and recording said medical movie or still images contained in said medical movie captured between said calculated moments.

24. The medical image management method of claim 20, further including a step of simultaneously displaying said medical movie captured by said medical imaging device and said medical movie sampled according to said physiological data of said surgeon.

25. The medical image management method of claim 20, wherein obtaining said physiological data of said surgeon includes obtaining at least one parameter selected from a group consisting of said surgeon's heart beat, blood pressure, sweat production, body temperature, electroencephalogram, grip strength, point of gaze, blink, pupil, eye movement, respiratory rate (including apneic period), pneumogram, number of swallowing, skin electric conductance, electric potential difference of muscle, neurotransmitter level, blood glucose level, blood flow rate, blood composition, amount of various hormones, chewing pressure, electrocardiogram, galvanic skin reflex, fingertip pulse wave, posture or position, tear production, tear composition, saliva production, saliva composition, gastric secretion, gastric fluid composition, facial expression (measurement in characteristic analysis), vocal change (measurement in characteristic analysis), lip reading (measurement in characteristic analysis), limb shivering, and urine (protein level, sugar level, occult blood level).

26. The medical image management method of claim 20, wherein information about events that occur during medical treatment is saved in said medical movies.

27. The medical image management method of claim 20, further including a step of selecting a certain medical movie depending on the total number of the indices added to the medical movie.

28. The medical image management method of claim 20, further including a step of adding indices to said medical movies responsive to a command by said surgeon.

29. The medical image management method of claim 20, wherein said physiological data obtained from said surgeon includes grip strength or an electroencephalogram.

30. The medical image management method of claim 29, wherein said physiological data is obtained during a craniotomy.

31. The medical image management method of claim 29, wherein said physiological data is obtained during an ophthalmic surgery using a microscope.

32. The medical image management method of claim 20, wherein said step of adding indices to said medical movie according to said physiological data of said surgeon includes electronically analyzing said physiological data to determine locations of said indices.

* * * * *